(12) United States Patent
Ballotti et al.

(10) Patent No.: US 9,194,003 B2
(45) Date of Patent: Nov. 24, 2015

(54) MITF AS A MARKER FOR PREDISPOSITION TO CANCER

(75) Inventors: Robert Ballotti, Nice (FR); Corine Bertolotto, Nice (FR); Brigitte Bressac De Paillerets, Sceaux (FR); Mahaut De Lichy, Paris (FR); Fabienne Lesueur, Lyons (FR)

(73) Assignees: INSTITUT GUSTAVE ROUSSY, Villejuif (FR); INSERM (INSTITUT NATIONAL DE LA SANTE ET DE LA RECHERCHE MEDICALE), Paris (FR); UNIVERSITE SOPHIA NICE ANTIPOLIS, Nice (FR)

( * ) Notice: Subject to any disclaimer, the term of this patent is extended or adjusted under 35 U.S.C. 154(b) by 0 days.

(21) Appl. No.: 13/515,984

(22) PCT Filed: Dec. 21, 2010

(86) PCT No.: PCT/FR2010/052853
§ 371 (c)(1),
(2), (4) Date: Jun. 14, 2012

(87) PCT Pub. No.: WO2011/083253
PCT Pub. Date: Jul. 14, 2011

(65) Prior Publication Data
US 2012/0252904 A1    Oct. 4, 2012

(30) Foreign Application Priority Data
Dec. 21, 2009    (FR) ...................................... 09 59325

(51) Int. Cl.
*C12Q 1/68* (2006.01)

(52) U.S. Cl.
CPC ........ *C12Q 1/6886* (2013.01); *C12Q 2600/106* (2013.01); *C12Q 2600/156* (2013.01)

(58) Field of Classification Search
None
See application file for complete search history.

(56) References Cited

PUBLICATIONS

King et al (American Journal of Pathology, 1999, 155(3): 731-738).*
Dorvault et al (Cancer, 2001, 93(5): 337-343).*
Sheffield et al (Am J Clin Pathol, 2002, 118(6): 930-936).*
Caltagirone et al (Int J Cancer, 2000, 87(4): 595-600).*
Cronin et al (Pigment Cell Melanoma Res, 2009, 22: 435-444).*
Samuels et al (Cancer Cell, 2005, 7(6): 561-573).*
Tockman et al (Cancer Res., 1992, 52:2711s-2718s).*
Cronin, J. C. et al. "Frequent mutations in the MITF pathway in melanoma" *Pigment Cell Melanoma Research*, Aug. 2009, pp. 435-444, vol. 22, No. 4.
Yokoyama, S. et al. "MITF pathway mutations in melanoma" *Pigment Cell Melanoma Research*, Aug. 2009, pp. 376-377, vol. 22, No. 4.
Murakami, H. et al. "Sumoylation modulates transcriptional activity of MITF in a promoter-specific manner" *Pigment Cell Research*, Aug. 2005, pp. 265-277, vol. 18, No. 4.
Miller, A. et al. "Sumoylation of MITF and Its Related Family Members TFE3 and TFEB" *The Journal of Biological Chemistry*, Jan. 7, 2005, pp. 146-155, vol. 280, No. 1.
Nihal, M. et al. "Anti-proliferative and proapoptotic effects of (-)-epigallocatechin-3-gallate on human melanoma: Possible implications for the chemoprevention of melanoma" *International Journal of Cancer*, Apr. 2005, pp. 513-521, vol. 114, No. 4.
Written Opinion in International Application No. PCT/FR2010/052853, May 16, 2011, pp. 1-7.

* cited by examiner

*Primary Examiner* — Sean Aeder
(74) *Attorney, Agent, or Firm* — Saliwanchik, Lloyd & Eisenschenk

(57) ABSTRACT

The present invention relates to a mutant of MITF which is useful as a marker for predisposition to the development of cancer and to uses thereof in diagnosis and preventive treatments, sumoylation being reduced or absent in this mutant.

13 Claims, 7 Drawing Sheets

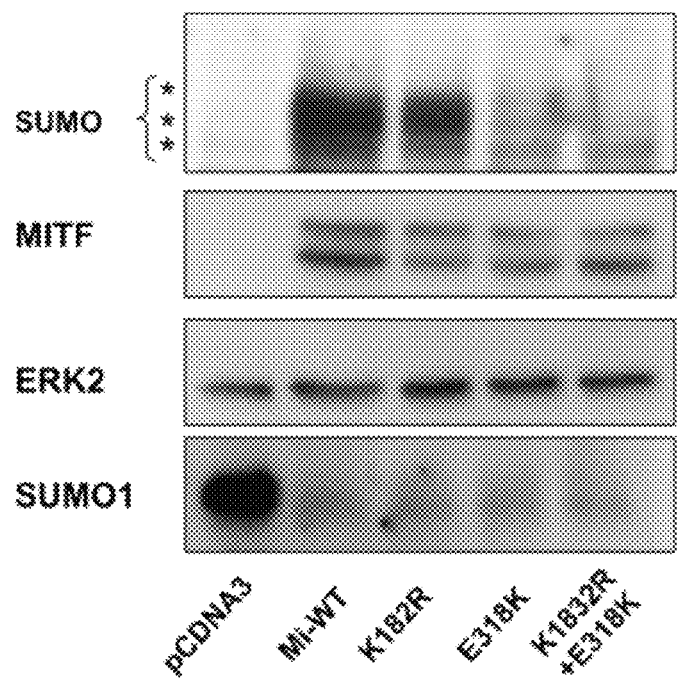
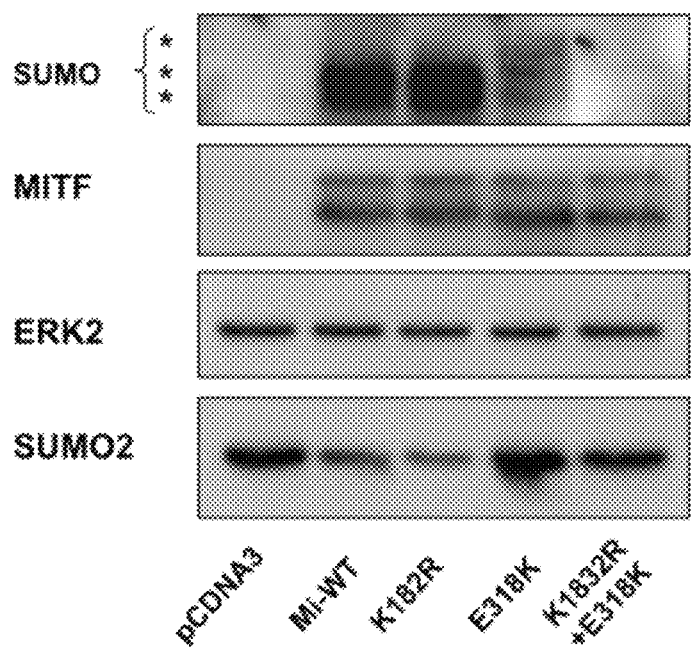
Figure 3

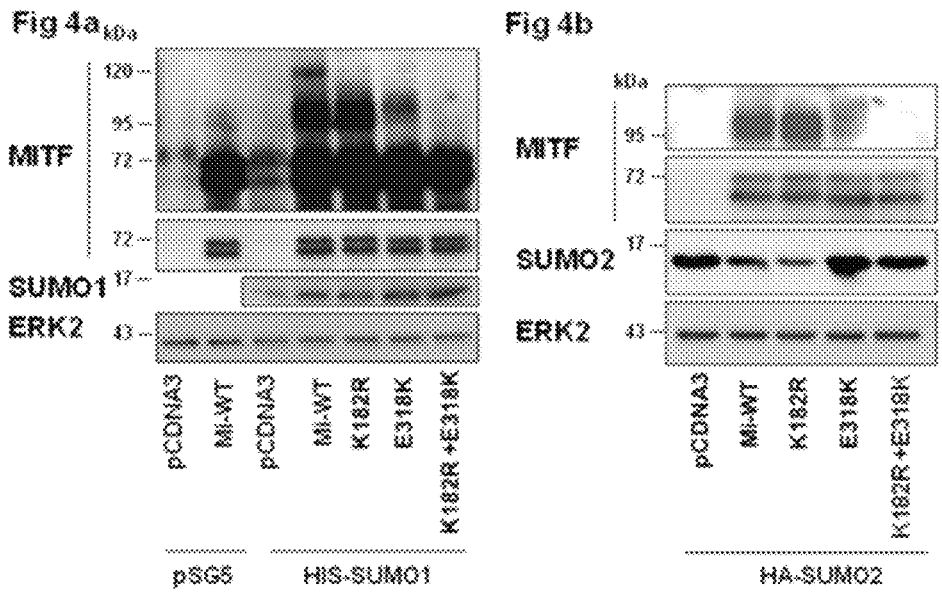
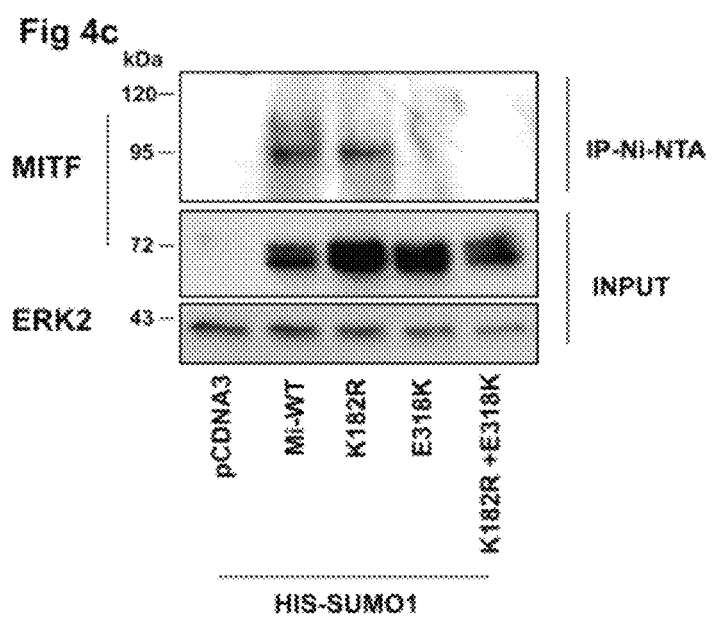

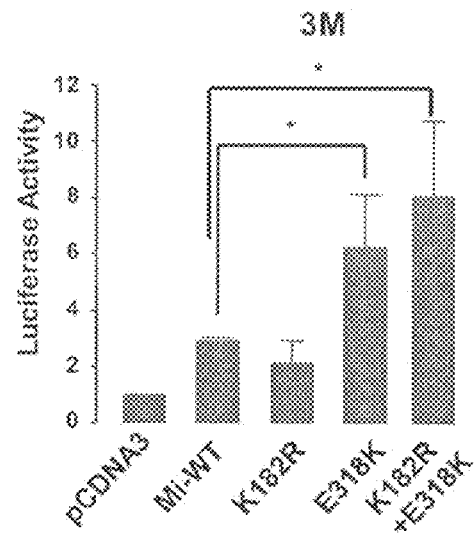
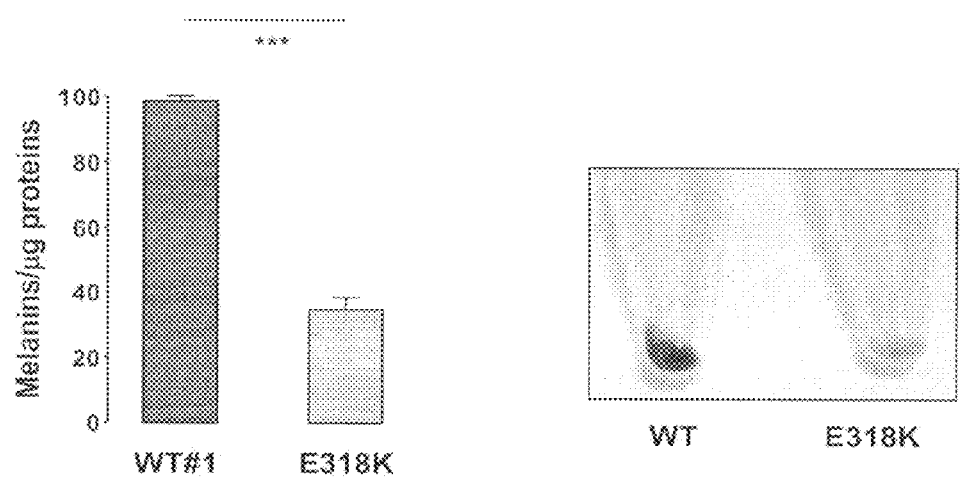
Figure 6

SEQUENCE LISTING

```
<160> NUMBER OF SEQ ID NOS: 40

<210> SEQ ID NO 1
<211> LENGTH: 20
<212> TYPE: DNA
<213> ORGANISM: artificial sequence
<220> FEATURE:
<223> OTHER INFORMATION: primer

<400> SEQUENCE: 1
cttgaagcaa gtggggagag                                                   20

<210> SEQ ID NO 2
<211> LENGTH: 21
<212> TYPE: DNA
<213> ORGANISM: artificial sequence
<220> FEATURE:
<223> OTHER INFORMATION: primer

<400> SEQUENCE: 2
ccactgctgg aaagtgagaa c                                                 21

<210> SEQ ID NO 3
<211> LENGTH: 18
<212> TYPE: DNA
<213> ORGANISM: artificial sequence
<220> FEATURE:
<223> OTHER INFORMATION: primer

<400> SEQUENCE: 3
ccgggccgaa ctacagat                                                     18

<210> SEQ ID NO 4
<211> LENGTH: 19
<212> TYPE: DNA
<213> ORGANISM: artificial sequence
<220> FEATURE:
<223> OTHER INFORMATION: primer

<400> SEQUENCE: 4
cagagtggca gacgcagtg                                                    19

<210> SEQ ID NO 5
<211> LENGTH: 20
<212> TYPE: DNA
<213> ORGANISM: artificial sequence
<220> FEATURE:
<223> OTHER INFORMATION: primer

<400> SEQUENCE: 5
tcctctcctt ttgcttctga                                                   20
```

```
<210> SEQ ID NO 6
<211> LENGTH: 22
<212> TYPE: DNA
<213> ORGANISM: artificial sequence
<220> FEATURE:
<223> OTHER INFORMATION: primer

<400> SEQUENCE: 6
tgaacaagaa ccaaagattt ca                                              22

<210> SEQ ID NO 7
<211> LENGTH: 20
<212> TYPE: DNA
<213> ORGANISM: artificial sequence
<220> FEATURE:
<223> OTHER INFORMATION: primer

<400> SEQUENCE: 7
cacagccagt gccagaacta                                                 20

<210> SEQ ID NO 8
<211> LENGTH: 22
<212> TYPE: DNA
<213> ORGANISM: artificial sequence
<220> FEATURE:
<223> OTHER INFORMATION: primer

<400> SEQUENCE: 8
cccaataaac ccttctcttc ct                                              22

<210> SEQ ID NO 9
<211> LENGTH: 20
<212> TYPE: DNA
<213> ORGANISM: Artificial sequence
<220> FEATURE:
<223> OTHER INFORMATION: primer

<400> SEQUENCE: 9
ggtgcaattt aggatacccc                                                 20

<210> SEQ ID NO 10
<211> LENGTH: 21
<212> TYPE: DNA
<213> ORGANISM: Artificial sequence
<220> FEATURE:
<223> OTHER INFORMATION: primer

<400> SEQUENCE: 10
cacctagcaa atggaaaatg g                                               21

<210> SEQ ID NO 11
<211> LENGTH: 20
<212> TYPE: DNA
<213> ORGANISM: Artificial sequence
<220> FEATURE:
<223> OTHER INFORMATION: primer

<400> SEQUENCE: 11
ggcccttatg tgaacgtttt                                                 20

<210> SEQ ID NO 12
<211> LENGTH: 22
<212> TYPE: DNA
<213> ORGANISM: Artificial sequence
<220> FEATURE:
<223> OTHER INFORMATION: primer
```

```
<400> SEQUENCE: 12
tggcatcaaa taataaacag ca                                              22

<210> SEQ ID NO 13
<211> LENGTH: 20
<212> TYPE: DNA
<213> ORGANISM: Artificial sequence
<220> FEATURE:
<223> OTHER INFORMATION: primer

<400> SEQUENCE: 13
tttgtgcctg aaggaagagc                                                 20

<210> SEQ ID NO 14
<211> LENGTH: 20
<212> TYPE: DNA
<213> ORGANISM: Artificial sequence
<220> FEATURE:
<223> OTHER INFORMATION: primer

<400> SEQUENCE: 14
caaaggctgg taaatgtggc                                                 20

<210> SEQ ID NO 15
<211> LENGTH: 20
<212> TYPE: DNA
<213> ORGANISM: Artificial sequence
<220> FEATURE:
<223> OTHER INFORMATION: primer

<400> SEQUENCE: 15
gttcatcttg ttgctgtgcc                                                 20

<210> SEQ ID NO 16
<211> LENGTH: 23
<212> TYPE: DNA
<213> ORGANISM: Artificial sequence
<220> FEATURE:
<223> OTHER INFORMATION: primer

<400> SEQUENCE: 16
gcttaagttt tcaggaaggt gtg                                             23

<210> SEQ ID NO 17
<211> LENGTH: 21
<212> TYPE: DNA
<213> ORGANISM: Artificial sequence
<220> FEATURE:
<223> OTHER INFORMATION: primer

<400> SEQUENCE: 17
aaagaccatt attgctttgg g                                               21

<210> SEQ ID NO 18
<211> LENGTH: 20
<212> TYPE: DNA
<213> ORGANISM: Artificial sequence
<220> FEATURE:
<223> OTHER INFORMATION: primer

<400> SEQUENCE: 18
aaaagaaccc tggaaacacc                                                 20

<210> SEQ ID NO 19
<211> LENGTH: 27
```

```
<212> TYPE: DNA
<213> ORGANISM: Artificial sequence
<220> FEATURE:
<223> OTHER INFORMATION: primer

<400> SEQUENCE: 19
ggagatcctg tacctctctt ttaatac                                    27

<210> SEQ ID NO 20
<211> LENGTH: 22
<212> TYPE: DNA
<213> ORGANISM: Artificial sequence
<220> FEATURE:
<223> OTHER INFORMATION: primer

<400> SEQUENCE: 20
tgttttaacc actgcagaga cc                                         22

<210> SEQ ID NO 21
<211> LENGTH: 24
<212> TYPE: DNA
<213> ORGANISM: Artificial sequence
<220> FEATURE:
<223> OTHER INFORMATION: primer

<400> SEQUENCE: 21
caaataagct tctgtatgtt tggg                                       24

<210> SEQ ID NO 22
<211> LENGTH: 22
<212> TYPE: DNA
<213> ORGANISM: Artificial sequence
<220> FEATURE:
<223> OTHER INFORMATION: primer

<400> SEQUENCE: 22
cagctgtagg aatcaactct cc                                         22

<210> SEQ ID NO 23
<211> LENGTH: 20
<212> TYPE: DNA
<213> ORGANISM: Artificial sequence
<220> FEATURE:
<223> OTHER INFORMATION: primer

<400> SEQUENCE: 23
aggttcaggt ttccgttgtc                                            20

<210> SEQ ID NO 24
<211> LENGTH: 20
<212> TYPE: DNA
<213> ORGANISM: Artificial sequence
<220> FEATURE:
<223> OTHER INFORMATION: primer

<400> SEQUENCE: 24
tagaaccaaa gggagagggg                                            20

<210> SEQ ID NO 25
<211> LENGTH: 18
<212> TYPE: DNA
<213> ORGANISM: Artificial sequence
<220> FEATURE:
<223> OTHER INFORMATION: primer

<400> SEQUENCE: 25
```
tacacggctt gggtggtg                                                         18

<210> SEQ ID NO 26
<211> LENGTH: 21
<212> TYPE: DNA
<213> ORGANISM: Artificial sequence
<220> FEATURE:
<223> OTHER INFORMATION: primer

<400> SEQUENCE: 26
catgtccaag aatgactgtg g                                                     21

<210> SEQ ID NO 27
<211> LENGTH: 23
<212> TYPE: DNA
<213> ORGANISM: artificial sequence
<220> FEATURE:
<223> OTHER INFORMATION: primer

<400> SEQUENCE: 27
gcttaaaagt cctctgtgct ctg                                                   23

<210> SEQ ID NO 28
<211> LENGTH: 22
<212> TYPE: DNA
<213> ORGANISM: artificial sequence
<220> FEATURE:
<223> OTHER INFORMATION: primer

<400> SEQUENCE: 28
caagaaaacc ccttcaggta ag                                                    22

<210> SEQ ID NO 29
<211> LENGTH: 16
<212> TYPE: DNA
<213> ORGANISM: artificial sequence
<220> FEATURE:
<223> OTHER INFORMATION: probe

<400> SEQUENCE: 29
atcaagcaag aacccg                                                           16

<210> SEQ ID NO 30
<211> LENGTH: 14
<212> TYPE: DNA
<213> ORGANISM: artificial sequence
<220> FEATURE:
<223> OTHER INFORMATION: probe

<400> SEQUENCE: 30
caagcaaaaa cccg                                                             14

<210> SEQ ID NO 31
<211> LENGTH: 23
<212> TYPE: DNA
<213> ORGANISM: artificial sequence
<220> FEATURE:
<223> OTHER INFORMATION: primer

<400> SEQUENCE: 31
tgctctccag atttggtgaa tcg                                                   23

<210> SEQ ID NO 32
<211> LENGTH: 21
<212> TYPE: DNA
<213> ORGANISM: artificial sequence

```
<220> FEATURE:
<223> OTHER INFORMATION: primer

<400> SEQUENCE: 32
ggtcttggct gcagttctca a                                              21

<210> SEQ ID NO 33
<211> LENGTH: 29
<212> TYPE: DNA
<213> ORGANISM: artificial sequence
<220> FEATURE:
<223> OTHER INFORMATION: primer

<400> SEQUENCE: 33
cttcccaaca taagaaggga gctcacagc                                       29

<210> SEQ ID NO 34
<211> LENGTH: 29
<212> TYPE: DNA
<213> ORGANISM: artificial sequence
<220> FEATURE:
<223> OTHER INFORMATION: primer

<400> SEQUENCE: 34
ggatcatcaa gcaaaaacca gttcttgag                                       29

<210> SEQ ID NO 35
<211> LENGTH: 520
<212> TYPE: PRT
<213> ORGANISM: Homo sapiens
<220> FEATURE:
<221> NAME/KEY: SITE
<222> LOCATION: (289)..(289)
<223> OTHER INFORMATION: Xaa = any amino acid
<220> FEATURE:
<221> NAME/KEY: SITE
<222> LOCATION: (291)..(291)
<223> OTHER INFORMATION: Xaa = any amino acid
<220> FEATURE:
<221> NAME/KEY: SITE
<222> LOCATION: (417)..(417)
<223> OTHER INFORMATION: Xaa = any amino acid
<220> FEATURE:
<221> NAME/KEY: SITE
<222> LOCATION: (419)..(419)
<223> OTHER INFORMATION: Xaa = any amino acid

<400> SEQUENCE: 35

Met Gln Ser Glu Ser Gly Ile Val Pro Asp Phe Glu Val Gly Glu Glu
1               5                   10                  15

Phe His Glu Glu Pro Lys Thr Tyr Tyr Glu Leu Lys Ser Gln Pro Leu
            20                  25                  30

Lys Ser Ser Ser Ser Ala Glu His Pro Gly Ala Ser Lys Pro Pro Ile
        35                  40                  45

Ser Ser Ser Ser Met Thr Ser Arg Ile Leu Leu Arg Gln Gln Leu Met
    50                  55                  60

Arg Glu Gln Met Gln Glu Gln Glu Arg Arg Glu Gln Gln Lys Leu
65                  70                  75                  80

Gln Ala Ala Gln Phe Met Gln Gln Arg Val Pro Val Ser Gln Thr Pro
                85                  90                  95

Ala Ile Asn Val Ser Val Pro Thr Thr Leu Pro Ser Ala Thr Gln Val
            100                 105                 110

Pro Met Glu Val Leu Lys Val Gln Thr His Leu Glu Asn Pro Thr Lys
        115                 120                 125
```

Tyr His Ile Gln Gln Ala Gln Arg Gln Val Lys Gln Tyr Leu Ser
130                 135                 140

Thr Thr Leu Ala Asn Lys His Ala Asn Gln Val Leu Ser Leu Pro Cys
145                 150                 155                 160

Pro Asn Gln Pro Gly Asp His Val Met Pro Val Pro Gly Ser Ser
                165                 170                 175

Ala Pro Asn Ser Pro Met Ala Met Leu Thr Leu Asn Ser Asn Cys Glu
                180                 185                 190

Lys Glu Gly Phe Tyr Lys Phe Glu Glu Gln Asn Arg Ala Glu Ser Glu
                195                 200                 205

Cys Pro Gly Met Asn Thr His Ser Arg Ala Ser Cys Met Gln Met Asp
210                 215                 220

Asp Val Ile Asp Ile Ile Ser Leu Glu Ser Ser Tyr Asn Glu Glu
225                 230                 235                 240

Ile Leu Gly Leu Met Asp Pro Ala Leu Gln Met Ala Asn Thr Leu Pro
                245                 250                 255

Val Ser Gly Asn Leu Ile Asp Leu Tyr Gly Asn Gln Gly Leu Pro Pro
                260                 265                 270

Pro Gly Leu Thr Ile Ser Asn Ser Cys Pro Ala Asn Leu Pro Asn Ile
                275                 280                 285

Xaa Arg Xaa Leu Thr Glu Ser Glu Ala Arg Ala Leu Ala Lys Glu Arg
290                 295                 300

Gln Lys Lys Asp Asn His Asn Leu Ile Glu Arg Arg Arg Phe Asn
305                 310                 315                 320

Ile Asn Asp Arg Ile Lys Glu Leu Gly Thr Leu Ile Pro Lys Ser Asn
                325                 330                 335

Asp Pro Asp Met Arg Trp Asn Lys Gly Thr Ile Leu Lys Ala Ser Val
                340                 345                 350

Asp Tyr Ile Arg Lys Leu Gln Arg Glu Gln Gln Arg Ala Lys Glu Leu
                355                 360                 365

Glu Asn Arg Gln Lys Lys Leu Glu His Ala Asn Arg His Leu Leu Leu
370                 375                 380

Arg Ile Gln Glu Leu Glu Met Gln Ala Arg Ala His Gly Leu Ser Leu
385                 390                 395                 400

Ile Pro Ser Thr Gly Leu Cys Ser Pro Asp Leu Val Asn Arg Ile Ile
                405                 410                 415

Xaa Gln Xaa Pro Val Leu Glu Asn Cys Ser Gln Asp Leu Leu Gln His
                420                 425                 430

His Ala Asp Leu Thr Cys Thr Thr Thr Leu Asp Leu Thr Asp Gly Thr
                435                 440                 445

Ile Thr Phe Asn Asn Asn Leu Gly Thr Gly Thr Glu Ala Asn Gln Ala
450                 455                 460

Tyr Ser Val Pro Thr Lys Met Gly Ser Lys Leu Glu Asp Ile Leu Met
465                 470                 475                 480

Asp Asp Thr Leu Ser Pro Val Gly Val Thr Asp Pro Leu Leu Ser Ser
                485                 490                 495

Val Ser Pro Gly Ala Ser Lys Thr Ser Ser Arg Arg Ser Ser Met Ser
                500                 505                 510

Met Glu Glu Thr Glu His Thr Cys
                515                 520

<210> SEQ ID NO 36
<211> LENGTH: 504
<212> TYPE: PRT

```
<213> ORGANISM: Homo sapiens
<220> FEATURE:
<221> NAME/KEY: SITE
<222> LOCATION: (273)..(273)
<223> OTHER INFORMATION: Xaa = any amino acid
<220> FEATURE:
<221> NAME/KEY: SITE
<222> LOCATION: (275)..(275)
<223> OTHER INFORMATION: Xaa = any amino acid
<220> FEATURE:
<221> NAME/KEY: SITE
<222> LOCATION: (401)..(401)
<223> OTHER INFORMATION: Xaa = any amino acid
<220> FEATURE:
<221> NAME/KEY: SITE
<222> LOCATION: (403)..(403)
<223> OTHER INFORMATION: Xaa = any amino acid

<400> SEQUENCE: 36
```

Met Glu Ala Leu Arg Val Gln Met Phe Met Pro Cys Ser Phe Glu Ser
1               5                   10                  15

Leu Tyr Leu Ser Ser Ala Glu His Pro Gly Ala Ser Lys Pro Pro Ile
            20                  25                  30

Ser Ser Ser Ser Met Thr Ser Arg Ile Leu Leu Arg Gln Gln Leu Met
        35                  40                  45

Arg Glu Gln Met Gln Glu Gln Glu Arg Arg Glu Gln Gln Gln Lys Leu
    50                  55                  60

Gln Ala Ala Gln Phe Met Gln Gln Arg Val Pro Val Ser Gln Thr Pro
65                  70                  75                  80

Ala Ile Asn Val Ser Val Pro Thr Thr Leu Pro Ser Ala Thr Gln Val
                85                  90                  95

Pro Met Glu Val Leu Lys Val Gln Thr His Leu Glu Asn Pro Thr Lys
            100                 105                 110

Tyr His Ile Gln Gln Ala Gln Arg Gln Gln Val Lys Gln Tyr Leu Ser
        115                 120                 125

Thr Thr Leu Ala Asn Lys His Ala Asn Gln Val Leu Ser Leu Pro Cys
    130                 135                 140

Pro Asn Gln Pro Gly Asp His Val Met Pro Pro Val Pro Gly Ser Ser
145                 150                 155                 160

Ala Pro Asn Ser Pro Met Ala Met Leu Thr Leu Asn Ser Asn Cys Glu
                165                 170                 175

Lys Glu Gly Phe Tyr Lys Phe Glu Glu Gln Asn Arg Ala Glu Ser Glu
            180                 185                 190

Cys Pro Gly Met Asn Thr His Ser Arg Ala Ser Cys Met Gln Met Asp
        195                 200                 205

Asp Val Ile Asp Asp Ile Ile Ser Leu Glu Ser Ser Tyr Asn Glu Glu
    210                 215                 220

Ile Leu Gly Leu Met Asp Pro Ala Leu Gln Met Ala Asn Thr Leu Pro
225                 230                 235                 240

Val Ser Gly Asn Leu Ile Asp Leu Tyr Gly Asn Gln Gly Leu Pro Pro
                245                 250                 255

Pro Gly Leu Thr Ile Ser Asn Ser Cys Pro Ala Asn Leu Pro Asn Ile
            260                 265                 270

Xaa Arg Xaa Leu Thr Glu Ser Glu Ala Arg Ala Leu Ala Lys Glu Arg
        275                 280                 285

Gln Lys Lys Asp Asn His Asn Leu Ile Glu Arg Arg Arg Phe Asn
    290                 295                 300

Ile Asn Asp Arg Ile Lys Glu Leu Gly Thr Leu Ile Pro Lys Ser Asn
305                 310                 315                 320

```
Asp Pro Asp Met Arg Trp Asn Lys Gly Thr Ile Leu Lys Ala Ser Val
            325                 330                 335

Asp Tyr Ile Arg Lys Leu Gln Arg Glu Gln Gln Arg Ala Lys Glu Leu
            340                 345                 350

Glu Asn Arg Gln Lys Lys Leu Glu His Ala Asn Arg His Leu Leu Leu
            355                 360                 365

Arg Ile Gln Glu Leu Glu Met Gln Ala Arg Ala His Gly Leu Ser Leu
370                 375                 380

Ile Pro Ser Thr Gly Leu Cys Ser Pro Asp Leu Val Asn Arg Ile Ile
385                 390                 395                 400

Xaa Gln Xaa Pro Val Leu Glu Asn Cys Ser Gln Asp Leu Leu Gln His
            405                 410                 415

His Ala Asp Leu Thr Cys Thr Thr Thr Leu Asp Leu Thr Asp Gly Thr
            420                 425                 430

Ile Thr Phe Asn Asn Asn Leu Gly Thr Gly Thr Glu Ala Asn Gln Ala
            435                 440                 445

Tyr Ser Val Pro Thr Lys Met Gly Ser Lys Leu Glu Asp Ile Leu Met
            450                 455                 460

Asp Asp Thr Leu Ser Pro Val Gly Val Thr Asp Pro Leu Leu Ser Ser
465                 470                 475                 480

Val Ser Pro Gly Ala Ser Lys Thr Ser Ser Arg Arg Ser Ser Met Ser
            485                 490                 495

Met Glu Glu Thr Glu His Thr Cys
            500

<210> SEQ ID NO 37
<211> LENGTH: 519
<212> TYPE: PRT
<213> ORGANISM: Homo sapiens
<220> FEATURE:
<221> NAME/KEY: SITE
<222> LOCATION: (288)..(288)
<223> OTHER INFORMATION: Xaa = any amino acid
<220> FEATURE:
<221> NAME/KEY: SITE
<222> LOCATION: (290)..(290)
<223> OTHER INFORMATION: Xaa = any amino acid
<220> FEATURE:
<221> NAME/KEY: SITE
<222> LOCATION: (416)..(416)
<223> OTHER INFORMATION: Xaa = any amino acid
<220> FEATURE:
<221> NAME/KEY: SITE
<222> LOCATION: (418)..(418)
<223> OTHER INFORMATION: Xaa = any amino acid

<400> SEQUENCE: 37

Met Gly His Leu Glu Asn Thr Ser Val Val Phe Pro Arg Ala Ile Phe
1               5                   10                  15

Ser Leu Cys Glu Lys Glu Thr Arg Lys Leu Thr Leu Cys Leu Phe Ser
            20                  25                  30

Arg Ser Ser Ser Ala Glu His Pro Gly Ala Ser Lys Pro Pro Ile Ser
        35                  40                  45

Ser Ser Ser Met Thr Ser Arg Ile Leu Leu Arg Gln Gln Leu Met Arg
    50                  55                  60

Glu Gln Met Gln Glu Gln Glu Arg Arg Glu Gln Gln Lys Leu Gln
65                  70                  75                  80

Ala Ala Gln Phe Met Gln Gln Arg Val Pro Val Ser Gln Thr Pro Ala
                85                  90                  95
```

-continued

```
Ile Asn Val Ser Val Pro Thr Thr Leu Pro Ser Ala Thr Gln Val Pro
            100                 105                 110
Met Glu Val Leu Lys Val Gln Thr His Leu Glu Asn Pro Thr Lys Tyr
        115                 120                 125
His Ile Gln Gln Ala Gln Arg Gln Gln Val Lys Gln Tyr Leu Ser Thr
    130                 135                 140
Thr Leu Ala Asn Lys His Ala Asn Gln Val Leu Ser Leu Pro Cys Pro
145                 150                 155                 160
Asn Gln Pro Gly Asp His Val Met Pro Val Pro Gly Ser Ser Ala
                165                 170                 175
Pro Asn Ser Pro Met Ala Met Leu Thr Leu Asn Ser Asn Cys Glu Lys
            180                 185                 190
Glu Gly Phe Tyr Lys Phe Glu Glu Gln Asn Arg Ala Glu Ser Glu Cys
        195                 200                 205
Pro Gly Met Asn Thr His Ser Arg Ala Ser Cys Met Gln Met Asp Asp
    210                 215                 220
Val Ile Asp Asp Ile Ile Ser Leu Glu Ser Ser Tyr Asn Glu Glu Ile
225                 230                 235                 240
Leu Gly Leu Met Asp Pro Ala Leu Gln Met Ala Asn Thr Leu Pro Val
                245                 250                 255
Ser Gly Asn Leu Ile Asp Leu Tyr Gly Asn Gln Gly Leu Pro Pro Pro
            260                 265                 270
Gly Leu Thr Ile Ser Asn Ser Cys Pro Ala Asn Leu Pro Asn Ile Xaa
        275                 280                 285
Arg Xaa Leu Thr Glu Ser Glu Ala Arg Ala Leu Ala Lys Glu Arg Gln
    290                 295                 300
Lys Lys Asp Asn His Asn Leu Ile Glu Arg Arg Arg Arg Phe Asn Ile
305                 310                 315                 320
Asn Asp Arg Ile Lys Glu Leu Gly Thr Leu Ile Pro Lys Ser Asn Asp
                325                 330                 335
Pro Asp Met Arg Trp Asn Lys Gly Thr Ile Leu Lys Ala Ser Val Asp
            340                 345                 350
Tyr Ile Arg Lys Leu Gln Arg Glu Gln Gln Arg Ala Lys Glu Leu Glu
        355                 360                 365
Asn Arg Gln Lys Lys Leu Glu His Ala Asn Arg His Leu Leu Leu Arg
    370                 375                 380
Ile Gln Glu Leu Glu Met Gln Ala Arg Ala His Gly Leu Ser Leu Ile
385                 390                 395                 400
Pro Ser Thr Gly Leu Cys Ser Pro Asp Leu Val Asn Arg Ile Ile Xaa
                405                 410                 415
Gln Xaa Pro Val Leu Glu Asn Cys Ser Gln Asp Leu Leu Gln His His
            420                 425                 430
Ala Asp Leu Thr Cys Thr Thr Thr Leu Asp Leu Thr Asp Gly Thr Ile
        435                 440                 445
Thr Phe Asn Asn Asn Leu Gly Thr Gly Thr Glu Ala Asn Gln Ala Tyr
    450                 455                 460
Ser Val Pro Thr Lys Met Gly Ser Lys Leu Glu Asp Ile Leu Met Asp
465                 470                 475                 480
Asp Thr Leu Ser Pro Val Gly Val Thr Asp Pro Leu Leu Ser Ser Val
                485                 490                 495
Ser Pro Gly Ala Ser Lys Thr Ser Ser Arg Arg Ser Ser Met Ser Met
            500                 505                 510
Glu Glu Thr Glu His Thr Cys
```

-continued

```
            515

<210> SEQ ID NO 38
<211> LENGTH: 419
<212> TYPE: PRT
<213> ORGANISM: Homo sapiens
<220> FEATURE:
<221> NAME/KEY: SITE
<222> LOCATION: (182)..(182)
<223> OTHER INFORMATION: Xaa = any amio acid
<220> FEATURE:
<221> NAME/KEY: SITE
<222> LOCATION: (184)..(184)
<223> OTHER INFORMATION: Xaa = any amio acid
<220> FEATURE:
<221> NAME/KEY: SITE
<222> LOCATION: (316)..(316)
<223> OTHER INFORMATION: Xaa = any amio acid
<220> FEATURE:
<221> NAME/KEY: SITE
<222> LOCATION: (318)..(318)
<223> OTHER INFORMATION: Xaa = any amio acid

<400> SEQUENCE: 38

Met Leu Glu Met Leu Glu Tyr Asn His Tyr Gln Val Gln Thr His Leu
1               5                  10                  15

Glu Asn Pro Thr Lys Tyr His Ile Gln Gln Ala Gln Arg Gln Gln Val
            20                  25                  30

Lys Gln Tyr Leu Ser Thr Thr Leu Ala Asn Lys His Ala Asn Gln Val
        35                  40                  45

Leu Ser Leu Pro Cys Pro Asn Gln Pro Gly Asp His Val Met Pro Pro
    50                  55                  60

Val Pro Gly Ser Ser Ala Pro Asn Ser Pro Met Ala Met Leu Thr Leu
65                  70                  75                  80

Asn Ser Asn Cys Glu Lys Glu Gly Phe Tyr Lys Phe Glu Glu Gln Asn
                85                  90                  95

Arg Ala Glu Ser Glu Cys Pro Gly Met Asn Thr His Ser Arg Ala Ser
            100                 105                 110

Cys Met Gln Met Asp Asp Val Ile Asp Asp Ile Ile Ser Leu Glu Ser
        115                 120                 125

Ser Tyr Asn Glu Glu Ile Leu Gly Leu Met Asp Pro Ala Leu Gln Met
    130                 135                 140

Ala Asn Thr Leu Pro Val Ser Gly Asn Leu Ile Asp Leu Tyr Gly Asn
145                 150                 155                 160

Gln Gly Leu Pro Pro Pro Gly Leu Thr Ile Ser Asn Ser Cys Pro Ala
                165                 170                 175

Asn Leu Pro Asn Ile Xaa Arg Xaa Leu Thr Ala Cys Ile Phe Pro Thr
            180                 185                 190

Glu Ser Glu Ala Arg Ala Leu Ala Lys Glu Arg Gln Lys Lys Asp Asn
        195                 200                 205

His Asn Leu Ile Glu Arg Arg Arg Phe Asn Ile Asn Asp Arg Ile
    210                 215                 220

Lys Glu Leu Gly Thr Leu Ile Pro Lys Ser Asn Asp Pro Asp Met Arg
225                 230                 235                 240

Trp Asn Lys Gly Thr Ile Leu Lys Ala Ser Val Asp Tyr Ile Arg Lys
                245                 250                 255

Leu Gln Arg Glu Gln Gln Arg Ala Lys Glu Leu Glu Asn Arg Gln Lys
            260                 265                 270

Lys Leu Glu His Ala Asn Arg His Leu Leu Leu Arg Ile Gln Glu Leu
        275                 280                 285
```

```
Glu Met Gln Ala Arg Ala His Gly Leu Ser Leu Ile Pro Ser Thr Gly
    290                 295                 300

Leu Cys Ser Pro Asp Leu Val Asn Arg Ile Ile Xaa Gln Xaa Pro Val
305                 310                 315                 320

Leu Glu Asn Cys Ser Gln Asp Leu Leu Gln His His Ala Asp Leu Thr
                325                 330                 335

Cys Thr Thr Thr Leu Asp Leu Thr Asp Gly Thr Ile Thr Phe Asn Asn
            340                 345                 350

Asn Leu Gly Thr Gly Thr Glu Ala Asn Gln Ala Tyr Ser Val Pro Thr
        355                 360                 365

Lys Met Gly Ser Lys Leu Glu Asp Ile Leu Met Asp Asp Thr Leu Ser
    370                 375                 380

Pro Val Gly Val Thr Asp Pro Leu Leu Ser Ser Val Ser Pro Gly Ala
385                 390                 395                 400

Ser Lys Thr Ser Ser Arg Arg Ser Ser Met Ser Met Glu Glu Thr Glu
                405                 410                 415

His Thr Cys

<210> SEQ ID NO 39
<211> LENGTH: 413
<212> TYPE: PRT
<213> ORGANISM: Homo sapiens
<220> FEATURE:
<221> NAME/KEY: SITE
<222> LOCATION: (182)..(182)
<223> OTHER INFORMATION: Xaa = any amino acid
<220> FEATURE:
<221> NAME/KEY: SITE
<222> LOCATION: (184)..(184)
<223> OTHER INFORMATION: Xaa = any amino acid
<220> FEATURE:
<221> NAME/KEY: SITE
<222> LOCATION: (310)..(310)
<223> OTHER INFORMATION: Xaa = any amino acid
<220> FEATURE:
<221> NAME/KEY: SITE
<222> LOCATION: (312)..(312)
<223> OTHER INFORMATION: Xaa = any amino acid

<400> SEQUENCE: 39

Met Leu Glu Met Leu Glu Tyr Asn His Tyr Gln Val Gln Thr His Leu
1               5                   10                  15

Glu Asn Pro Thr Lys Tyr His Ile Gln Gln Ala Gln Arg Gln Gln Val
                20                  25                  30

Lys Gln Tyr Leu Ser Thr Thr Leu Ala Asn Lys His Ala Asn Gln Val
            35                  40                  45

Leu Ser Leu Pro Cys Pro Asn Gln Pro Gly Asp His Val Met Pro Pro
        50                  55                  60

Val Pro Gly Ser Ser Ala Pro Asn Ser Pro Met Ala Met Leu Thr Leu
65                  70                  75                  80

Asn Ser Asn Cys Glu Lys Glu Gly Phe Tyr Lys Phe Glu Glu Gln Asn
                85                  90                  95

Arg Ala Glu Ser Glu Cys Pro Gly Met Asn Thr His Ser Arg Ala Ser
                100                 105                 110

Cys Met Gln Met Asp Asp Val Ile Asp Asp Ile Ile Ser Leu Glu Ser
            115                 120                 125

Ser Tyr Asn Glu Glu Ile Leu Gly Leu Met Asp Pro Ala Leu Gln Met
        130                 135                 140

Ala Asn Thr Leu Pro Val Ser Gly Asn Leu Ile Asp Leu Tyr Gly Asn
```

```
                  145                 150                 155                 160
        Gln Gly Leu Pro Pro Gly Leu Thr Ile Ser Asn Ser Cys Pro Ala
                        165                 170                 175

Asn Leu Pro Asn Ile Xaa Arg Xaa Leu Thr Glu Ser Glu Ala Arg Ala
                    180                 185                 190

Leu Ala Lys Glu Arg Gln Lys Lys Asp Asn His Asn Leu Ile Glu Arg
                195                 200                 205

Arg Arg Arg Phe Asn Ile Asn Asp Arg Ile Lys Glu Leu Gly Thr Leu
            210                 215                 220

Ile Pro Lys Ser Asn Asp Pro Asp Met Arg Trp Asn Lys Gly Thr Ile
        225                 230                 235                 240

Leu Lys Ala Ser Val Asp Tyr Ile Arg Lys Leu Gln Arg Glu Gln Gln
                        245                 250                 255

Arg Ala Lys Glu Leu Glu Asn Arg Gln Lys Lys Leu Glu His Ala Asn
                    260                 265                 270

Arg His Leu Leu Leu Arg Ile Gln Glu Leu Glu Met Gln Ala Arg Ala
                275                 280                 285

His Gly Leu Ser Leu Ile Pro Ser Thr Gly Leu Cys Ser Pro Asp Leu
            290                 295                 300

Val Asn Arg Ile Ile Xaa Gln Xaa Pro Val Leu Glu Asn Cys Ser Gln
        305                 310                 315                 320

Asp Leu Leu Gln His His Ala Asp Leu Thr Cys Thr Thr Thr Leu Asp
                        325                 330                 335

Leu Thr Asp Gly Thr Ile Thr Phe Asn Asn Asn Leu Gly Thr Gly Thr
                    340                 345                 350

Glu Ala Asn Gln Ala Tyr Ser Val Pro Thr Lys Met Gly Ser Lys Leu
                355                 360                 365

Glu Asp Ile Leu Met Asp Asp Thr Leu Ser Pro Val Gly Val Thr Asp
            370                 375                 380

Pro Leu Leu Ser Ser Val Ser Pro Gly Ala Ser Lys Thr Ser Ser Arg
        385                 390                 395                 400

Arg Ser Ser Met Ser Met Glu Glu Thr Glu His Thr Cys
                        405                 410

<210> SEQ ID NO 40
<211> LENGTH: 357
<212> TYPE: PRT
<213> ORGANISM: Homo sapiens
<220> FEATURE:
<221> NAME/KEY: SITE
<222> LOCATION: (126)..(126)
<223> OTHER INFORMATION: Xaa = any amino acid
<220> FEATURE:
<221> NAME/KEY: SITE
<222> LOCATION: (128)..(128)
<223> OTHER INFORMATION: Xaa = any amino acid
<220> FEATURE:
<221> NAME/KEY: SITE
<222> LOCATION: (254)..(254)
<223> OTHER INFORMATION: Xaa = any amino acid
<220> FEATURE:
<221> NAME/KEY: SITE
<222> LOCATION: (256)..(256)
<223> OTHER INFORMATION: Xaa = any amino acid

<400> SEQUENCE: 40

Met Leu Glu Met Leu Glu Tyr Asn His Tyr Gln Val Gln Thr His Leu
1               5                   10                  15

Glu Asn Pro Thr Lys Tyr His Ile Gln Gln Ala Gln Arg Gln Gln Gly
                20                  25                  30
```

-continued

```
Phe Tyr Lys Phe Glu Glu Gln Asn Arg Ala Glu Ser Glu Cys Pro Gly
        35                  40                  45
Met Asn Thr His Ser Arg Ala Ser Cys Met Gln Met Asp Asp Val Ile
 50                  55                  60
Asp Asp Ile Ile Ser Leu Glu Ser Ser Tyr Asn Glu Glu Ile Leu Gly
 65                  70                  75                  80
Leu Met Asp Pro Ala Leu Gln Met Ala Asn Thr Leu Pro Val Ser Gly
                 85                  90                  95
Asn Leu Ile Asp Leu Tyr Gly Asn Gln Gly Leu Pro Pro Pro Gly Leu
                100                 105                 110
Thr Ile Ser Asn Ser Cys Pro Ala Asn Leu Pro Asn Ile Xaa Arg Xaa
                115                 120                 125
Leu Thr Glu Ser Glu Ala Arg Ala Leu Ala Lys Glu Arg Gln Lys Lys
                130                 135                 140
Asp Asn His Asn Leu Ile Glu Arg Arg Arg Arg Phe Asn Ile Asn Asp
145                 150                 155                 160
Arg Ile Lys Glu Leu Gly Thr Leu Ile Pro Lys Ser Asn Asp Pro Asp
                165                 170                 175
Met Arg Trp Asn Lys Gly Thr Ile Leu Lys Ala Ser Val Asp Tyr Ile
                180                 185                 190
Arg Lys Leu Gln Arg Glu Gln Gln Arg Ala Lys Glu Leu Glu Asn Arg
                195                 200                 205
Gln Lys Lys Leu Glu His Ala Asn Arg His Leu Leu Leu Arg Ile Gln
        210                 215                 220
Glu Leu Glu Met Gln Ala Arg Ala His Gly Leu Ser Leu Ile Pro Ser
225                 230                 235                 240
Thr Gly Leu Cys Ser Pro Asp Leu Val Asn Arg Ile Ile Xaa Gln Xaa
                245                 250                 255
Pro Val Leu Glu Asn Cys Ser Gln Asp Leu Leu Gln His His Ala Asp
                260                 265                 270
Leu Thr Cys Thr Thr Thr Leu Asp Leu Thr Asp Gly Thr Ile Thr Phe
        275                 280                 285
Asn Asn Asn Leu Gly Thr Gly Thr Glu Ala Asn Gln Ala Tyr Ser Val
        290                 295                 300
Pro Thr Lys Met Gly Ser Lys Leu Glu Asp Ile Leu Met Asp Asp Thr
305                 310                 315                 320
Leu Ser Pro Val Gly Val Thr Asp Pro Leu Leu Ser Ser Val Ser Pro
                325                 330                 335
Gly Ala Ser Lys Thr Ser Ser Arg Arg Ser Ser Met Ser Met Glu Glu
                340                 345                 350
Thr Glu His Thr Cys
                355
```

MITF AS A MARKER FOR PREDISPOSITION TO CANCER

CROSS-REFERENCE TO RELATED APPLICATION

This application is the U.S. national stage application of International Patent Application No. PCT/FR2010/052853, filed Dec. 21, 2010, the disclosure of which is hereby incorporated by reference in its entirety, including all figures, tables and amino acid or nucleic acid sequences.

The present application relates to the field of medicine, and more particularly to that of determining a predisposition to the development of cancer.

In approximately 5% of cancers, constitutional mutations that activate oncogenes or inactivate tumor suppressor genes (known as major genes or strong effect genes) confer a high risk (>50% lifetime risk) of developing cancer to the individuals who carry them, and are responsible for familial forms of cancer, cancers with an early age of onset, or multiple primary cancers. The expression of the disease may vary under the influence of other genetic factors (known as modifiers, or weak effect genes) or environmental factors. Identifying individuals at risk allows them to benefit from prevention and surveillance aimed at early detection. In some cases, the constitutional germline mutation can guide the anticancer therapy, as in the case of anti-PARP treatments in patients with BRCA1 and BRCA2 germline mutations (Hennessy B. T. J., JCO, 2010, 28, 3570-3576).

Melanoma is a malignant tumor of melanocytes. It is one of the rarest forms of skin cancer but accounts for the majority of skin cancer deaths. Despite many years of intensive research, the only effective treatment is surgical resection of the primary tumor before it reaches a thickness of more than 1 mm. According to a WHO report, there are approximately 48,000 melanoma deaths per year. Some studies have speculated that patients with cutaneous melanoma may have an increased risk of developing breast cancer, lymphoma or kidney cancer.

In melanoma, two strong effect genes have been identified to date: CDKN2A coding for the p16$^{INK4A}$ and p14$^{ARF}$ proteins, and CDK4. The major environmental factor is UV exposure. Known weak effect genes are mainly those which encode proteins involved in skin pigmentation, MC1R being the most widely studied to date. In 50% of families with three melanoma cases, no susceptibility gene has been identified.

In this context, the inventors have studied the MITF gene, a major regulatory gene of melanocytes (1) and an oncogene (2,3), as a candidate gene predisposing to melanoma. MITF is a transcription factor from the bHLH-LZ family which plays a major role in melanocyte survival and growth. MITF is involved in the regulation of melanogenesis. The role of MITF is unusual in that it both induces and represses cell proliferation. Indeed, this factor is necessary for terminal melanocyte differentiation and/or pigmentation, on the one hand, and for malignant behavior by inducing cell proliferation, on the other hand. Constitutional "loss of function" mutations of the MITF gene are associated with autosomal dominant diseases such as Waardenburg syndrome and Tietz syndrome, characterized by hearing loss and pigmentation anomalies of the skin, hair and/or iris.

The MITF gene comprises 9 exons. Six MITF isoforms have been identified. In humans they are generally referred to as isoforms 1 to 6, while isoform 4 is more commonly known as isoform M. In the mouse, the letter nomenclature is used instead. These isoforms are transcribed by specific promoters. In addition, they can be distinguished by their N-terminal region and all contain exons 2 to 9, whereas exon 1 is specific of each isoform (1). Isoform 4, more commonly known as MITF-M, differs from the other isoforms by an insertion of six amino acids. This isoform has been detected only in melanocytes or in vivo transformed cells (nevus, melanoma, etc.) or in vitro cell lines. The other isoforms are expressed in many tissues and cell lines, sometimes also with tissue specificities.

WO 00/47765 teaches that alternative splicing of the MITF gene produces mitf+ and mitf− transcripts coding for proteins differing by the insertion of six additional amino acids in mitf+. mitf+ and mitf− are predominantly expressed in healthy and tumor cells, respectively. This patent application therefore discloses a semi-quantitative method for evaluating, predicting or monitoring the risk and the treatment of melanoma. WO 05/116249 also describes a quantitative method based on these MITF splicing variants.

In the present invention, the inventors have identified a recurrent germline mutation in the MITF gene, herein named E318K (based on the nomenclature of isoform 4), which is useful as a marker for predisposition to cancer.

The MITF gene (microphthalmia-associated transcription factor) is well known to one of skill in the art and can be characterized by its references in data bases such as UniGene (Hs.166017), HomoloGene (4892) and GeneID (4286). It is also called MI, WS2A or bHLHe32.

Said E318K mutation maps to exon 9 of the MITF gene, in particular to position 952 of isoform M according to HGVS nomenclature. It corresponds to a substitution of a nucleotide G by a nucleotide A (c.952G>A) in the coding sequence and results in the substitution of a glutamic acid by a lysine (p.Glu318Lys). Exon 9 is common to all MITF splicing variants. In the MITF-M isoform, this residue is in position 952 of the transcript and results in the mutation of the amino acid in position 318. The term "E318K mutation" designates the mutation, regardless of its position in the MITF isoforms. In particular, the position of the mutated nucleotide and the amino acid in the different splicing variants is shown below.

| Isoform | Other name | Transcript ref. | Protein ref. | Mutation | SEQ ID No |
|---|---|---|---|---|---|
| ISOFORM 1 | MITF-A | NM_198159 | NP_937802 | E419K | 35 |
| ISOFORM 2 | MITF-H | NM_198177 | NP_937820 | E403K | 36 |
| ISOFORM 3 | MITF-C | NM_006722 | NP_006713 | E418K | 37 |
| ISOFORM 4 | MITF-M | NM_000248 | NP_000239 | E318K | 38 |
| ISOFORM 5 |  | NM_198158 | NP_937801 | E312K | 39 |
| ISOFORM 6 |  | NM_198178 | NP_937821 | E394K | 40 |

The MITF E318K mutant is more potent than wild-type MITF at activating transcription of the HIF1A gene, known to play a major role in renal carcinogenesis (secondarily activated with "loss of function" mutations of genes predisposing to kidney cancer, such as VHL, FH, SDHB). Furthermore, it has been shown that this mutation reduces sumoylation of MITF, thereby perhaps influencing the stability of the protein or the amount of proteins coded by the target genes. In fact, amino acid E318 is part of one of the two sumoylation sites in the MITF protein. As the MITF gene encodes a transcription factor, the MITF E318K mutant protein may continuously activate some of its target genes. It is also possible that the mutation changes the localization of the MITF protein or its nuclear-cytoplasmic ratio.

The inventors have discovered that the MITF E318K mutant is more frequent in patients with cutaneous malignant melanoma and concomitant kidney cancer. The mutation is also thought to be more frequent in individuals who developed cutaneous malignant melanoma and kidney cancer or in families with a history of melanoma and kidney cancer in relatives, or cutaneous melanoma and another cancer, in particular a polycythemia or a lymphoma. This mutant is present at a very low frequency (2/2846 subjects, i.e., a frequency of heterozygotes of 0.0007 in a first cohort, and 11/1824 subjects, i.e., a frequency of heterozygotes of 0.003 in a second cohort) in healthy control subjects. The inventors have shown that the non-sumoylated form of MITF leads to less differentiated melanocytes and more highly proliferative cells.

Moreover, it is likely that this mutant is also more frequent in subjects having developed one or more tumors originating in the neural crest such as a neuroendocrine cancer, a sarcoma, a neuroblastoma or a nervous system tumor (NST), or other types of cancers according to the preliminary results of the inventors, such as a lymphoma, a lung cancer, a kidney cancer, a breast cancer, a pancreatic cancer, a pediatric tumor, a hematopoietic malignancy, a gastrointestinal cancer, a polycythemia or a combination of these types of cancer. The sumoylation sites classically comprise the W-K-X-E consensus motif in which W is a hydrophobic amino acid and X is any amino acid. MITF possesses two sumoylation sites: the first site has the sequence IKRE (with the K in positions 289, 273, 288, 182, 182 and 126, respectively, in isoforms 1, 2, 3, 4, 5 and 6), and the second site has the sequence IKQE (with the K in positions 417, 401, 416, 316, 310 and 254, respectively, in isoforms 1, 2, 3, 4, 5 and 6). The K182 and K316 mutations increase the transcription of a target gene, melastatin/TRPM, but do not affect DNA binding, localization or stability of the protein (Miller A J et al., JBC, 2005, 280: 146-155).

The teaching with regard to the MITF E318K mutant of the present invention may be generalized to any MITF mutation reducing or abolishing the sumoylation of the MITF protein at one of the sumoylation sites or at both sites.

Therefore, the present invention relates to a method for determining whether a subject has a predisposition or a susceptibility to develop a cancer selected from the group consisting of: a cutaneous malignant melanoma, a kidney cancer, a thyroid cancer, a sarcoma, a neuroblastoma, a central nervous system tumor (CNST), a lymphoma, a lung cancer, a polycythemia, and combinations thereof, comprising determining in a biological sample from the subject the presence of an MITF mutation (microphthalmia-associated transcription factor) reducing or abolishing the sumoylation of MITF, the presence of said mutation indicating that the subject has a predisposition or a susceptibility to develop such cancer. In a particular embodiment, notably when the MITF mutation is E318K (that is to say, E318K in isoform 4 or substitution of the corresponding Glu residue in the other MITF isoforms by a Lys residue), the cancer is a cutaneous malignant melanoma or a combination of a cutaneous malignant melanoma and another cancer, particularly a cancer selected from the group consisting of a neuroendocrine cancer, a sarcoma, a neuroblastoma or a nervous system tumor (NST), a lymphoma, a lung cancer, a kidney cancer, a breast cancer, a pancreatic cancer, a pediatric tumor, a hematopoietic malignancy, a gastrointestinal cancer, a polycythemia and combinations thereof. The cancer may also be selected from among a kidney cancer, a thyroid cancer, a sarcoma, a neuroblastoma, a central nervous system tumor (CNST), a lymphoma, a lung cancer, a polycythemia, and combinations thereof. In a particular embodiment, the combination is that of a cutaneous malignant melanoma and a kidney cancer.

Preferably, the mutation is a substitution of a lysine residue and/or of a glutamic acid residue of one of the MITF sumoylation sites or of both sites. For instance, the mutation is the substitution of a residue selected from the following table by any of the other 19 amino acids.

| Isoform | Transcript ref. | Protein ref. | 1$^{st}$ sumoylation site | | 2$^{nd}$ sumoylation site | |
|---|---|---|---|---|---|---|
| ISOFORM 1 | NM_198159 | NP_937802 | K289 | E291 | K417 | E419 |
| ISOFORM 2 | NM_198177 | NP_937820 | K273 | E275 | K401 | E403 |
| ISOFORM 3 | NM_006722 | NP_006713 | K288 | E290 | K416 | E418 |
| ISOFORM 4 | NM_000248 | NP_000239 | K182 | E184 | K316 | E318 |
| ISOFORM 5 | NM_198158 | NP_937801 | K182 | E184 | K310 | E312 |
| ISOFORM 6 | NM_198178 | NP_937821 | K126 | E128 | K254 | E256 |

More specifically, a lysine residue may be substituted by any of the other 19 amino acids; and/or, a glutamic acid residue may be substituted by any of the other 19 amino acids.

Preferably, the method comprises detecting a substitution of the "K316" residue (that is to say, K316 in isoform 4 or the corresponding Lys residue in the other MITF isoforms) and/or of the "E318" residue (that is to say, E318 in isoform 4 or the corresponding Glu residue in the other MITF isoforms) by any of the other 19 amino acids.

In a preferred embodiment, the method comprises detecting a substitution of the "E318" residue (that is to say, E318 in isoform 4 or the corresponding Glu residue in the other MITF isoforms) by any of the other 19 amino acids. In an even more preferred embodiment, the method comprises detecting the "E318K" mutation (that is to say, E318K in isoform 4 or the substitution of the corresponding Glu residue by a Lys residue in the other MITF isoforms).

The mutation may be detected at the protein or nucleic level. The methods for identifying the mutation such as defined earlier in the MITF gene or transcripts thereof (mRNA) are well known to one of skill in the art and include in particular and not by way of limitation, sequencing, selective hybridization and/or selective amplification. At the nucleic level, detection may be carried out on a sample of genomic DNA, mRNA or cDNA.

In particular, sequencing of MITF may be complete or partial. In fact, the method may comprise solely the sequencing of the region comprising the residue suspected to be mutated and even the sequencing of only this particular residue.

Selective hybridization is understood to mean that the genomic DNA, RNA or cDNA is placed in the presence of a probe specific of the mutant MITF and optionally a probe specific of MITF not harboring said mutation or wild-type MITF. The probes may be in suspension or immobilized on a substrate. Typically, the probes will be labeled for easier detection. In particular, the probes are single-stranded nucleic acid molecules of 8 to 1000 nucleotides, preferably 10 to 800 or 15 to 50 nucleotides.

The nucleic acid may be amplified before detection of the mutation. For instance, a primer pair specific of the regions flanking the position of the mutation to be detected (that is to say, upstream or downstream) will be constructed. Typically, the primers are single-stranded nucleic acid molecules of 5 to 60 nucleotides, preferably 8 to 25 nucleotides. Perfect complementarity is preferred because it ensures high specificity. However, some mismatches may be tolerated. Once the MITF gene or the exon containing the mutation, or else one of its transcripts, has been amplified, the amplicon is used for detecting the presence of the mutation by sequencing or specific hybridization or by any other suitable method known to one of skill in the art. The mutation may also be detected by melting curve analysis (see WO2007/035806 for example).

The presence of the mutation may also be detected by selective amplification of the mutant. For instance, a primer pair is prepared, one of the primers specifically hybridizing with the sequence carrying the mutation to be detected. Said primer will be able to initiate amplification or to hybridize with its target only if the sequence carries the mutated nucleotide. As a result, the presence of an amplicon would indicate that MITF harbors the tested mutation, whereas the absence of said amplicon would indicate that MITF does not harbor this mutation.

It shall be understood that these methods may be readily adapted by one of skill in the art to detect simultaneously or in parallel several mutations of the sumoylation site(s). Thus, the methods would allow the detection of one or more mutations coding for the substitution of residues selected from the group consisting of K182, E184, K316 and E318 in MITF isoform 4 or the corresponding residues in the other MITF isoforms.

When the mutation is detected at the protein level, the method makes use of an antibody able to discriminate between MITF harboring the mutation to be detected and MITF not harboring said mutation. In particular, the biological sample is contacted with an antibody directed against MITF harboring the mutation to be detected and the presence of an immune complex is detected. Different methods allow the detection of said immune complexes such as ELISA, radioimmunoassay (RIA) and immunoenzymatic assay (IEMA). "Antibody" also refers to any antibody fragments and derivatives conserving the ability to specifically bind to the MITF mutant to be detected as compared to MITF not harboring this mutation. Here again, these methods may be easily adapted by one of skill in the art for the simultaneous or in parallel detection of several mutations of one or more sumoylation site(s). Thus, the methods would allow the detection of one or more substitutions of residues selected from the group consisting of K182, E184, K316 and E318 in MITF isoform 4 or the corresponding residues in the other MITF isoforms, for example with the aid of a combination of antibodies specific for each MITF mutant harboring one or several of these substitutions.

Alternatively, the mutation reducing or abolishing MITF sumoylation may be detected at the protein level in an indirect manner. For instance, the presence of the mutation may be detected by measuring the sumoylation of MITF, a reduction of sumoylation relative to the wild-type MITF protein indicating the presence of the mutation. The examples describe how said sumoylation is measured. Likewise, the mutation reducing sumoylation, the mutant MITF protein is stabilized and therefore detectable in tissue slices by immunohistochemistry or immunofluorescence. Detection of the mutation or of the presence/absence of sumoylation may also be carried out by mass spectrometry (WO/2005/003390).

In a particularly interesting embodiment of the present invention, sumoylation of MITF is measured indirectly by determining the cellular localization of MITF detected by immunohistochemistry or immunofluorescence. In fact, in a surprising and highly original manner, the reduction of sumoylation of the MITF protein causes a modification of the cellular localization of the MITF protein visible by immunohistochemistry in tumor cells. The wild-type protein is located only or mainly in the nucleus whereas the protein harboring the mutation reducing sumoylation of the protein, in particular the E318K mutation, is located in both the nucleus and the cytoplasm. Thus, the present invention relates to a method wherein the mutation reducing sumoylation of MITF is detected by determining the cellular localization of MITF by immunohistochemistry, a nuclear localization indicating the wild-type MITF protein and a cytoplasmic localization indicating the MITF protein harboring a mutation reducing sumoylation of MITF, in particular the MITF E318K mutant. The mutation may also allow detection of the MITF protein by immunohistochemistry or immunofluorescence in tissues where the wild-type protein is undetectable by these same methods.

The mutation may be detected in any MITF isoform. In a particular embodiment, the mutation is detected in isoform 4.

In the spirit of the invention, the term "subject" refers to a mammal, preferably a human.

In the spirit of the invention, the term "biological sample" refers to a sample of healthy or tumor tissue, for example a biopsy and in particular a biopsy of the skin, kidney, thyroid, lung, or a biological fluid, for example a sample of blood, cerebrospinal fluid, urine or lymph. Preferably, the biological sample is a blood sample. The methods of the present invention may comprise a preliminary step of collecting the biological sample.

It shall be understood that the methods of the present invention also encompass, in addition to the detection of the mutation reducing or abolishing MITF sumoylation, the detection of other markers for predisposition to cancer.

The present invention also relates to the use of the means for detecting the mutation reducing or abolishing sumoylation of MITF for preparing a diagnostic kit for determining whether a subject has a predisposition or a susceptibility to develop a cancer selected from the following list: a cutaneous malignant melanoma, a neuroendocrine cancer, a sarcoma, a neuroblastoma or a nervous system tumor (NST), a lymphoma, a lung cancer, a kidney cancer, a breast cancer, a pancreatic cancer, a pediatric tumor, a hematopoietic malignancy, a gastrointestinal cancer, a polycythemia, and combinations thereof, the presence of said mutation indicating that the subject has a predisposition or a susceptibility to develop such cancer. In a particular embodiment, the cancer is selected from the group consisting of a cutaneous malignant melanoma, a kidney cancer, a thyroid cancer, a sarcoma, a neuroblastoma, a central nervous system tumor (CNST), a lymphoma, a lung cancer, a polycythemia and combinations thereof. In a preferred manner, the cancer is selected from among a cutaneous malignant melanoma, a kidney cancer and a combination thereof. The methods of detection may comprise or consist in a probe specific of MITF harboring the mutation to be detected, a primer pair allowing amplification of a nucleotide segment comprising the mutation to be detected, a pair of primers one of which specifically hybridizes with the sequence carrying the mutation to be detected (thereby allowing selective amplification of the MITF mutant to be detected), an antibody directed against the MITF mutant to be detected, means by which to detect and measure the sumoylation of MITF, negative controls for detecting MITF not carrying the mutation to be detected, or combinations thereof. In a particular embodiment, notably when the MITF mutation is E318K (that is to say, E318K in isoform 4 or the substitution of the corresponding Glu residue in the other MITF iso forms by a Lys residue), the cancer is a cutaneous malignant melanoma or a combination of a cutaneous malignant melanoma and another cancer, in particular a cancer selected from the group consisting of a neuroendocrine cancer, a sarcoma, a neuroblastoma or nervous system tumor (NST), a lymphoma, a lung cancer, a kidney cancer, a breast cancer, a pancreatic cancer, a pediatric tumor, a hematopoietic malignancy, a gastrointestinal cancer, a polycythemia, and combinations thereof. In a particular embodiment, the cancer is selected from the group consisting of a cutaneous malignant melanoma, a kidney cancer, a thyroid cancer, a sarcoma, a neuroblastoma, a central nervous system tumor (CNST), a lymphoma, a lung cancer, a polycythemia and combinations thereof. In a preferred manner, the cancer is selected from among a cutaneous malignant melanoma, a kidney cancer, and a combination thereof.

The interest of detecting a predisposition or a susceptibility to cancer is that the subject can benefit from clinical monitoring or surveillance allowing the detection of a cancer at an early stage and therefore increasing the chances of cure. Furthermore, detection of the mutation may make it possible to guide the therapeutic algorithm of the patient and/or enhance the efficacy of the treatments. Moreover, the subject so identified can also benefit from a preventive treatment. Said treatment is intended to prevent or delay the development of the cancer.

Thus, the present invention also relates to a method for selecting patients who may benefit from a preventive treatment or a medical surveillance comprising determining the patient's susceptibility to cancer by the method according to the present invention and selecting subjects presenting the mutation reducing or abolishing the sumoylation of MITF.

The preventive treatment in question may comprise administering polyphenolic compounds. In fact, it has been shown in particular that polyphenolic compounds from fermented rice hulls reduce the level of the MITF protein (5). Thus, said treatment might counteract the reduction of sumoylation of the MITF protein and its functional effects on its target genes, MITF being a transcription factor. Moreover, polyphenols from black tea have a chemopreventive action which might occur by cell cycle arrest and by a pro-apoptotic mechanism (6). Therefore, the present invention relates to polyphenolic compounds for a use in the preventive treatment of cancer in subjects carrying an MITF mutation reducing or abolishing the sumoylation of MITF and to the use of polyphenolic compounds for preparing a medicament intended for the preventive treatment of cancer (chemoprevention) in subjects carrying an MITF mutation reducing or abolishing the sumoylation of MITF. The invention further relates to a method of treatment comprising administering an effective therapeutic dose of polyphenolic compounds to subjects carrying an MITF mutation reducing or abolishing the sumoylation of MITF, thereby preventing or delaying the development of a cancer. Preferably, the polyphenolic compounds are polyphenolic compounds from fermented rice hulls or polyphenols from black tea. Patent application WO 05/099721 also describes many other polyphenolic compounds useful for the prevention of cancer, in particular through their antioxidant effect.

The invention will become clearer in the following examples which are given for purposes of illustration and not by way of limitation.

BRIEF DESCRIPTION OF DRAWINGS

FIG. 1: (FIG. 1b).

FIG. 3: Reduction of sumoylation of the MITF protein harboring the E318K mutation.

FIG. 4: The E318K mutation reduces sumoylation of the MITF protein. FIG. 4a) HEK293 cells were cotransfected with a plasmid coding for myc-tagged wild-type or mutant MITF (K182R; E318K; K182R/E318K) and pSG5His-SUMO1 or pSG5 empty vector. Cells were lysed in boiling buffer and tested by western blot for MITF and ERK2 to control for sufficient loading of each lane. FIG. 4b) HEK293 cells were cotransfected with a plasmid coding for myc-tagged wild-type or mutant MITF (K182R; E318K; K182R/E318K) and pSG5His-SUMO2 or pSG5 empty vector. Cells were tested by western blot for MITF and ERK2. FIG. 4c) HEK293 cells were cotransfected with a plasmid coding for myc-tagged wild-type or mutant MITF (K182R; E318K; K182R/E318K) and pSG5His-SUMO1 or pSg5 empty vector. Cell lysates were purified on Ni-NTA columns and analyzed by western blot for MITF (upper panel). The lower panel shows the western blot of cell lysates before purification to control MITF expression and sufficient loading of each lane.

FIG. 5: The E318K mutation might affect the cellular localization of MITF and alter its transcriptional activity.

FIG. 6: Mutant melanocytes show lighter pigmentation. Cell pellets and melanin determination in the melanocytes of two healthy donors compared with melanocytes isolated from a skin biopsy of patients harboring the E318K mutation (***) show a significant difference (p<0.001). The two donors and the mutant carriers were Caucasian.

EXAMPLES

Example 1

Figures 1A, 1B:
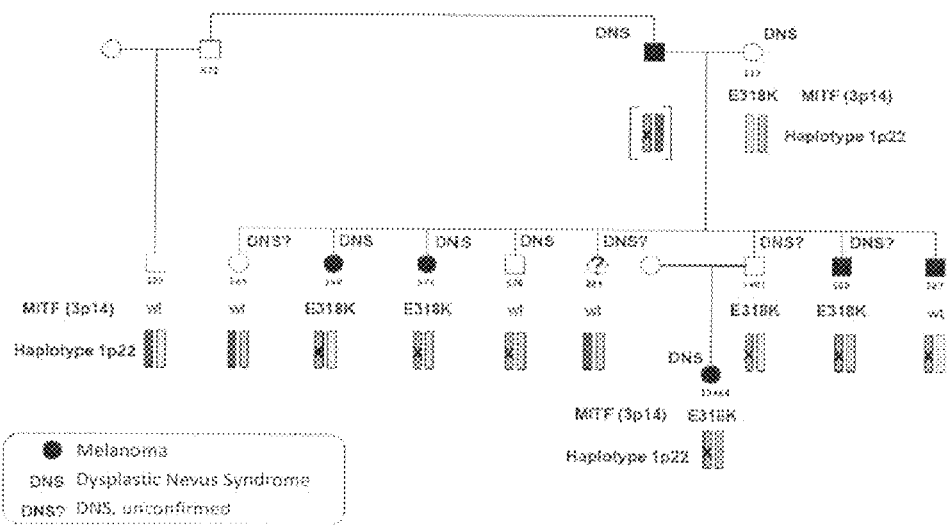
(FIG. 1a) Pedigree of the first family with multiple melanoma cases in which the MITF E318K variant was identified.
(FIG. 1b) electrophoregram of the germline mutation (blood) in a person with melanoma and kidney cancer.

The inventors studied the MITF gene, which is considered an oncogene and therefore a candidate gene. They first studied whether there were mutations in the MITF gene (3p14) at the caspase cleavage site (anti-apoptotic effect) in melanoma families (4), by sequencing all the isoforms. Their preliminary results revealed the presence of a germline variant of MITF-M c.952G>A, p.Glu318Lys (E318K) in a Spanish Basque family (TRY) with multiple cases of melanoma (with 2 kidney cancers, 3 central nervous system tumors, 1 lung cancer and 1 stomach cancer on the maternal side from whence the E318K mutation originated), with paternal transmission of a 1p22 haplotype. The variant was absent in 180 French/Caucasian and 96 Spanish Basque controls (FIGS. 1a and b).

Figure 2:
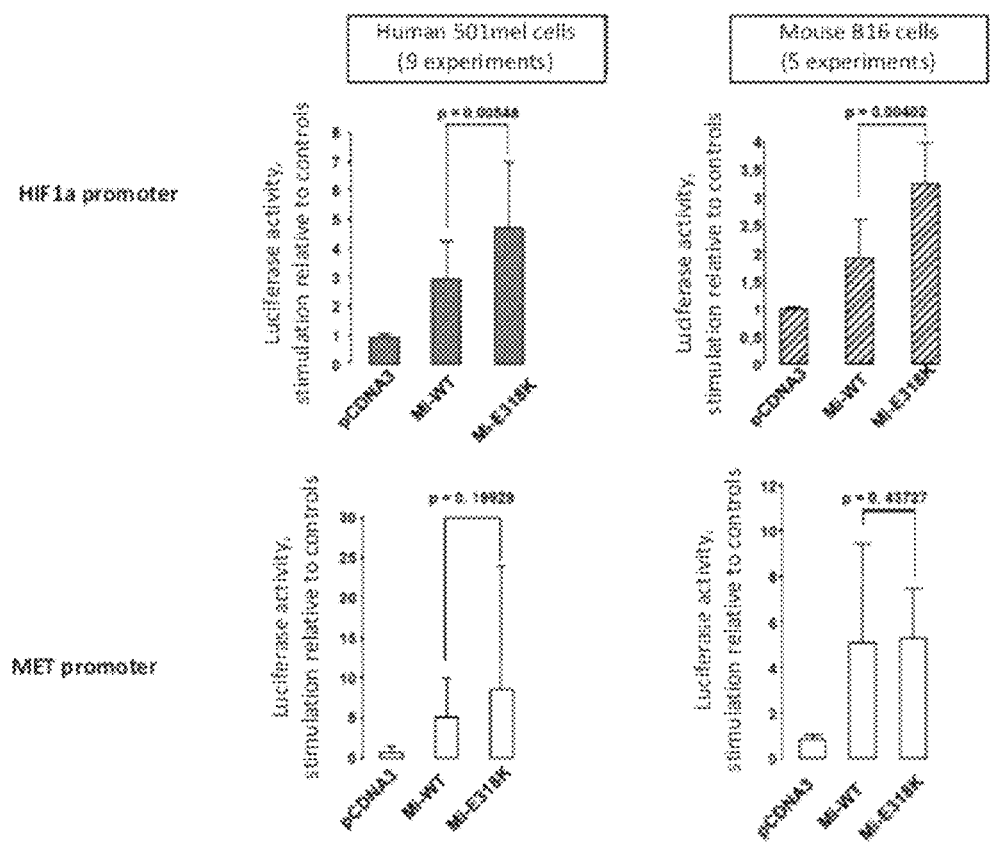
FIG. 2: Transcriptional activation of the HIF1A but not the MET promoter in the presence of the MITF protein harboring the E318K mutation compared with wild-type MITF protein.

In B16 mouse melanoma cells, the inventors showed that the MITF variant c.952G>A, p.Glu318Lys (E318K) was more active than the wild-type form at inducing transcription of the HIF1a gene but not of the MET gene (FIG. 2). The inventors therefore hypothesized that HIF is the transforming factor of renal cells in the absence of VHL, in hypoxic conditions; VHL (loss of function mutations of a tumor suppressor gene) and MET (activating mutations of an oncogene) are two genes predisposing to kidney cancer; HI1aF activated by the MITF E318K mutant might therefore have the same effect as absence of VHL. The inventors therefore showed that the MITF E318K mutation was present in 4/55 patients and absent in 276 controls (p=0.0007) of the "melanoma and renal cancer (sporadic cases)" subgroup of the MELARISK cohort. The inventors then investigated the frequency of the E318K mutant in the different biological sample collections of IGR (Institut Gustave Roussy, Villejuif, France). Other carriers of this mutation were identified: a female who developed juvenile TFE3 translocation-associated kidney cancer whose mother had breast cancer followed by melanoma; a female who developed 3 melanomas and a lymphoma; an index case of a family with multiple cases of melanoma; an index case who developed several melanomas; two males who developed nodular melanomas; a female who developed melanoma, one of whose uncles had a CNST; two males who developed a renal papillary carcinoma; a male with polycythemia. In fact, VHL is one of the three genes predisposing to polycythemia.

TABLE 1

Results of MITF E318K mutation screening

| Melanoma and renal cancer | Sample No. | MITF wild-type | MITF E318K | p-value |
|---|---|---|---|---|
| Sporadic | 55 | 51 | 4 | 0.0007 |
| Familial | 50 | 49 | 1 | 0.1534 |
| Sporadic and familial | 105 | 100 | 5 | 0.0015 |
| Papillary renal cancer | 24 | 22 | 2 | 0.0062 |
| Melanoma and CNST, familial | | | 1 | 0.1687 |
| Polycythemia | 14 | 13 | 1 | 0.0483 |
| Lymphoma | 16 | 15 | 1 | 0.0548 |
| Melanomas | | | | |
| Multiple melanomas Familial | 107 | 106 | 1 | 0.2794 |
| Multiple melanomas Sporadic | 34 | 33 | 1 | 0.1097 |
| Nodular melanomas | 90 | 88 | 2 | 0.0600 |

TABLE 1-continued

Results of MITF E318K mutation screening

| Melanoma and renal cancer | Sample No. | MITF wild-type | MITF E318K | p-value |
|---|---|---|---|---|
| Multiple cutaneous melanomas Familial | 49 | 48 | 1 | 0.1508 |

Control populations were blood and CEPH donors (N=276).

Example 2

Identification of MITF Germline Mutations in Patients with Melanoma and Renal Cell Carcinoma To confirm the identification of the MITF variant resulting from a missense substitution p.E318K (c.952G>A in MITF isoform M, NM_000248) associated with coexisting melanoma and renal cancer, the inventors sequenced the entire coding sequence of the gene, the intron-exon boundaries and the 8 alternative promoters in 62 patients with coexisting melanoma and renal cell carcinoma. This substitution was observed in 5 of the 62 patients. The frequency of this variant is significantly higher than in the control population of 1824 subjects (4% vs 0.3%, p=$9.7 \times 10^{-5}$). Thus, p.E318K carriers have a 14-fold higher risk of developing both melanoma and renal cell carcinoma (Odds Ratio=14.46 [95% confidence interval: 3.79-46.82]) (Table 2). To confirm that this variant affects the susceptibility to melanoma alone, the inventors genotyped 704 patients with melanoma (who were negative for the CDKN2A and CDK4 mutations predisposing to melanoma) including 422 independent cases with a family history of melanoma, 242 sporadic cases with multiple primary melanomas and 40 sporadic nodular melanomas (Table 2). The latter cases were tested because 4 of the 5 patients with both melanoma and renal cell carcinoma and carrying the p.E318K mutation had at least one nodular melanoma (the rarest histologic type of melanoma). The frequency of p.E318K was significantly higher in all patients with melanoma alone as compared to controls (1.3% vs 0.3%, p=$4.5 \times 10^{-5}$) and p.E318K carriers had a more than fourfold increased risk of developing melanoma (Odds Ratio=4.57 [95% confidence interval: 2.05-10.68]). This increased risk appears to be due mainly to the sporadic multiple primary melanoma patients (Odds Ratio=7.10 [95% confidence interval: 2.67-18.62]) whereas the effect of p.E318K was not significant for melanoma patients from a melanoma family (Odds Ratio=2.78 [95% confidence interval: 0.9-7.90]) or for patients with nodular melanoma (Odds Ratio=8.67 [95% confidence interval: 0.91-41.70] (Table 3)). However, the test of homogeneity of the frequency of the p.E318K allele across these three groups was only marginally significant (p=0.06). Biological material was available for additional affected family members in three of the seven melanoma families in which the proband carried the variant. In each of these families, p.E318K cosegregated with melanoma. Alternatively, to examine the effect of p.E318K on susceptibility to renal cancer, the inventors genotyped this variant in 187 patients with renal cell carcinoma. The frequency of p.E318K was also higher in patients with renal cancer than in controls (1.3% vs 0.3%, p=0.01) and the increase in the risk of renal cancer associated with p.E318K was similar to that seen for melanoma alone (Odds Ratio=4.53 [95% confidence interval:

1.22-14.30]) (Table 2). There was no significant demonstration of heterogeneity of the p.E318K allele frequency across the three groups of patients (melanoma+renal cell carcinoma, melanoma alone, renal cell carcinoma alone; p=0.08). Combining all the patient groups increased the degree of significance of the difference in p.E318K allele frequency between cases and controls (1.5% vs 0.3%, p=$2.5 \times 10^{-7}$). On the whole, carriers of the p.E318K mutation had a more than fivefold increased risk of developing melanoma, renal cell carcinoma or both (Odds Ratio=5.17 [95% confidence interval: 2.49-11.52]).

To determine whether p.E318K predisposes to the co-occurrence of melanoma and another cancer other than renal cancer, the investigators genotyped 172 patients with melanoma and another primary tumor but none carried the p.E318K mutation (Table 2). Since association of p.E318K with another primary tumor is a rare event, the inventors plan to study larger series.

TABLE 2

Frequency of the p.E318K germline mutation in patients with cancer

| Type of tumor | Number of non-carriers | Number of carriers* | Total | Minority allele frequency | FET p-value | OR [95% CI] |
|---|---|---|---|---|---|---|
| Controls | 1813 | 11 | 1824 | 0.003 | — | Ref |
| CM or/and RCC | 924 | 29 | 953 | 0.015 | $2.5 \times 10^{-7}$ | 5.17 [2.49-11.52] |
| Both | 57 | 5[a] | 62 | 0.040 | $9.7 \times 10^{-5}$ | 14.46 [3.79-46.82] |
| CM alone[b] | 685 | 19[c] | 704 | 0.013 | $4.5 \times 10^{-5}$ | 4.57 [2.05-10.68] |
| RCC alone[d] | 182 | 5[e] | 187 | 0.013 | 0.012 | 4.53 [1.22-14.30] |
| Melanoma and another cancer[f] | 172 | 0 | 172 | 0 | 0.61 | — |

OR = Odds Ratio;
95% CI = 95% confidence interval;
p-value = critical probability of the test;
CM = cutaneous melanoma;
RCC = renal cell carcinoma.
*All carriers are heterozygotes for the p.E318K variant.
[a]The 5 patients developed clear cell renal cell carcinoma (ccRCC), 4 of the 5 patients developed at least one nodular melanoma, and the 5th patient developed a superficial spreading melanoma (SSM).
[b]Familial melanomas (in particular with at least 2 confirmed melanoma cases in the family), 422 cases; sporadic cases with multiple primary melanomas (MPM), 242 cases; sporadic nodular melanoma, 40 cases.
[c]Out of 19 carriers, 7 are familial cases, 9 are sporadic MPM cases and 2 are sporadic nodular melanoma cases.
[d]Clear cell renal cell carcinoma (ccRCC), 54 sporadic cases; papillary renal cell carcinoma (PRC), 55 cases (22 cases with type I, 30 cases with type II, and 3 cases with unknown histologic subtype); mixed renal cell carcinoma phenotypes (in particular, papillary and clear cell), 2 cases; pediatric renal cell carcinoma, 5 cases; renal cell carcinoma with unknown histologic subtype, 71 cases.
[e]Out of 5 carriers, one is a clear cell renal cell carcinoma (ccRCC), 2 are type II papillary renal cell carcinomas, 1 is a juvenile carcinoma with a somatic translocation t(X; 17)(p11; q25) and 1 is a type I papillary renal cell carcinoma.
[f]Breast cancer, 97 cases; brain cancer, 27 cases; non-medullary thyroid cancer, 28 cases; colon cancer, 10 cases; other cancers (testicular, uterine, ovarian, prostate, sarcoma and endometrial), 10 cases.

Test of homogeneity of allele frequency among melanoma alone, renal cell carcinoma alone and the combination of the two: p=0.078 (exact test).

TABLE 3

Frequency of the MITF p.E318K germline mutation in patients with melanoma alone

| Type of tumor | Number of non-carriers | Number of carriers* | Total | Minority allele frequency | FET p-value | OR [95% CI] |
|---|---|---|---|---|---|---|
| Controls | 1813 | 11 | 1824 | 0.003 | — | Ref |
| CM alone | 685 | 19 | 704 | 0.013 | $4.5 \times 10^{-5}$ | 4.57 [2.05-10.68] |
| Familial | 415 | 7 | 422 | 0.008 | 0.06 | 2.78 [0.91-7.90] |
| Multiple primary melanoma (MPM) | 232 | 10 | 242 | 0.021 | $4.1 \times 10^{-5}$ | 7.10 [2.67-18.62] |
| Nodular melanoma | 38 | 2 | 40 | 0.025 | 0.029 | 8.67 [0.90-41.70] |

Test of homogeneity of allele frequency among the 3 categories of melanoma alone (familial, MPM, nodular): p = 0.065 (exact test).
Test of homogeneity comparing familial versus MPM: p = 0.072 (exact test)

Example 3

Functional Effects of the MITF p.E318K Mutation

This E318K mutation is located at one of the two sumoylation sites of the protein (WKXE motif, 2 sites K182 and K316). The inventors have demonstrated a reduction in sumoylation of MITF in the presence of the E318K mutation (FIG. 3).

More specifically, the inventors have produced the E318K variant by site directed mutagenesis. In addition, they have also prepared the K182R variant and a K182R:E318K double mutant.

After coexpression of His-SUMO-1 with wild-type MITF, western blots on total extracts using an anti-MITF antibody revealed the presence of a 120 kD band and a doublet of approximately 90 kD, suggesting that MITF undergoes sumoylation which increases its molecular weight (FIG. 4A). While addition of exogenous SUMO protein increased the overall level of MITF sumoylation, western blots revealed that MITF is also sumoylated in basal conditions showing the 90 kD doublet, thereby excluding a non-specific effect of SUMO overexpression. The K182R mutation led to complete disappearance of the higher molecular weight form of MITF but had practically no effect on the 90 kD band. When codon 318 was mutated to lysine, the inventors observed a considerable reduction in the level of all the high molecular weight bands of MITF. Lastly, no high molecular weight forms of MITF were observed when the double mutant was used. Similar results were seen with coexpression of HA-SUMO-2 (FIG. 4B), demonstrating that wild-type MITF was modified by SUMO-1 or SUMO-2 and that the E318K mutation affected both SUMO-1 and SUMO-2 modifications. To confirm SUMO-1 binding to MITF, the His-SUMO-1 plasmid was transfected alone or with the MITF constructs. Then, proteins containing His-SUMO-1 were purified on a Ni-TFA column. In cells transfected with wild-type MITF, the western blot with anti-MITF antibody revealed sumoylated forms of MITF migrating at approximately 90 and 120 kD (FIG. 4C). The K182R mutation mainly affected the 120 kD sumoylated form of MITF whereas no sumoylated form was found with E318K or the double mutant. Together, these results show that codon 316 is a major SUMO acceptor site in MITF and that the E318K mutation dramatically reduces sumoylation of MITF.

Example 4

Figure 5A:
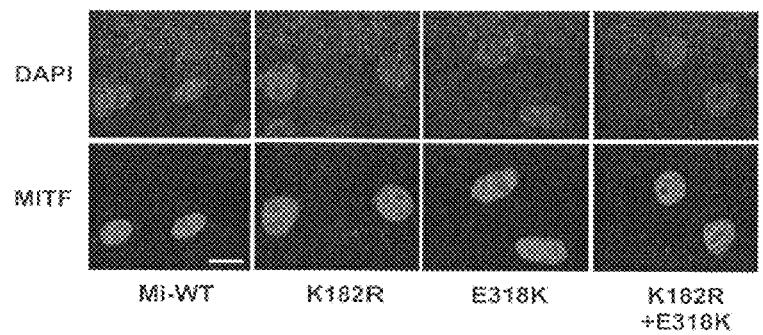
FIG. 5a) Immunofluorescence analysis of HEK293 cells transfected with a plasmid coding for myc-tagged wild-type or mutant MITF (K182R; E318K; K182R/E318K E318K) and stained with an anti-myc antibody, then stained secondarily with Alexafluor 594-labeled anti-mouse antibody. Cell nuclei were counterstained with DAPI. The bar represents 10 µm.
Figure 5B:
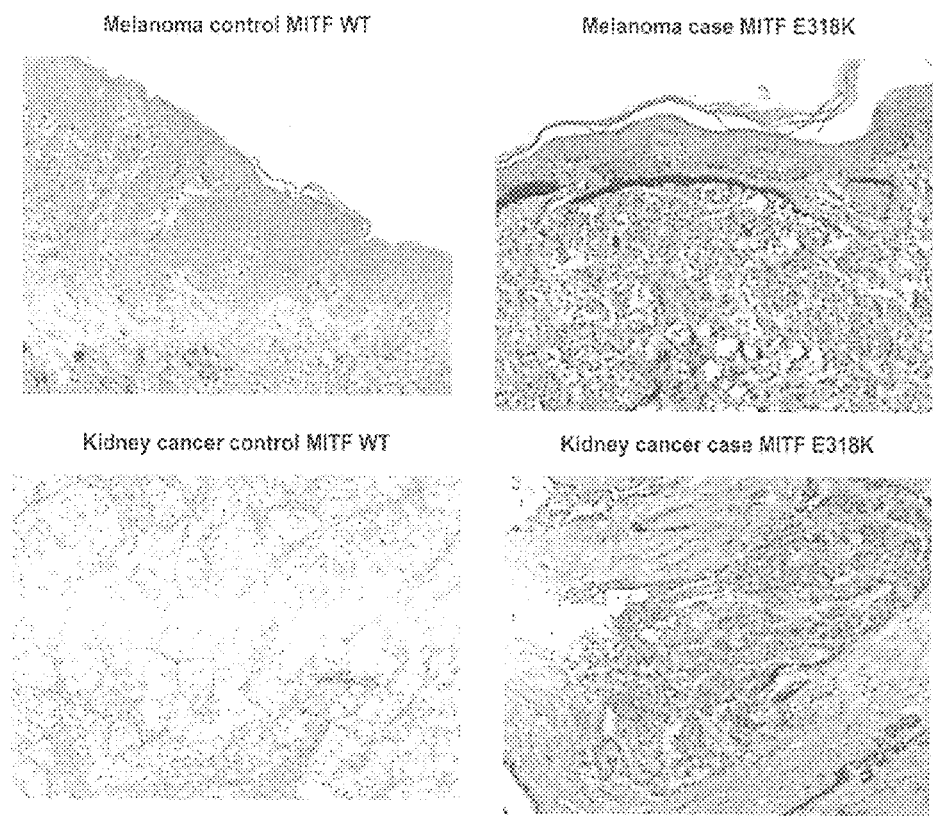
FIG. 5b) Immunohistochemical staining of melanoma and renal tumor tissue with anti-MITF antibody (×200). Melanoma harboring wild-type MITF show nuclear staining while melanoma harboring the MITF E318K mutation show nuclear and cytoplasmic staining Renal cancer tissue harboring wild-type MITF does not stain whereas renal cancer tissue harboring the MITF E318K mutation shows nuclear and cytoplasmic staining FIG. 5c) HEL293 cells were transiently transfected with a synthetic 3× M-box luciferase reporter plasmid and with the mutant or wild-type MITF pCDNA3 construct or empty pCDNA3 vector. Luciferase activity was normalized to β-galactosidase activity and the results were expressed as fold-stimulation over basal luciferase activity for unstimulated cells.

The E318K Mutation Might Change the Localization of MITF and Alters its Transcriptional Activity Sumoylation orchestrates many cellular processes, partly by controlling nuclear-cytoplasmic signal transduction and transcription. The inventors investigated whether the E318K mutant with reduced sumoylation could modify the cellular localization of MITF (FIG. 5A). Immunofluorescence staining with anti-MITF antibody showed that the E318K mutant but also the K182R and K182R:E318K mutants were detected in the nuclei of melanoma cells, which is consistent with the nuclear localization of wild-type MITF. However, immunohistochemistry experiments on melanoma and kidney cancer cells revealed that E318K mutants showed both nuclear and cytoplasmic staining (FIG. 5B).

| Type of staining | Nuclear | Nuclear + cytoplasmic | None |
|---|---|---|---|
| Control melanoma | 8/9 | 1/9 | 0/9 |
| Melanoma with E318K mutation | 0/8 | 8/8 | 0/8 |
| Control kidney cancer | 0/6 | 0/6 | 6/6 |
| Kidney cancer with E318K mutation | 0/6 | 2/6 | 4/6 |

The inventors also explored the possible effect of the E318K substitution on the transcriptional activity of MITF by comparing the activity of the wild-type versus E318K mutant on a synthetic reporter containing 3 copies M box linked to an SV40 minimal promoter. The E318K mutant had 2-3 times more transcriptional activity than the wild-type (FIG. 5C). The double mutant was even more active than the E318K mutant while the single mutant K182R had an activity similar to wild-type. These data indicate that sumoylation reduces the transcriptional activity of MITF. The inventors then checked the effect of the E318K mutation on physiological promoters, focusing on MET and HIF1A, two MITF target genes involved in melanocyte and renal carcinogenesis. Wild-type MITF and the E318K mutant had similar transcriptional activity on the MET promoter (FIG. 2) whereas the E318K mutant had higher transcriptional activity than wild-type on the HIF1A promoter. Therefore, the p.E318K mutation may exert its oncogenic effect through transcriptional up-regulation of HIF1A.

Example 5

Figure 7:
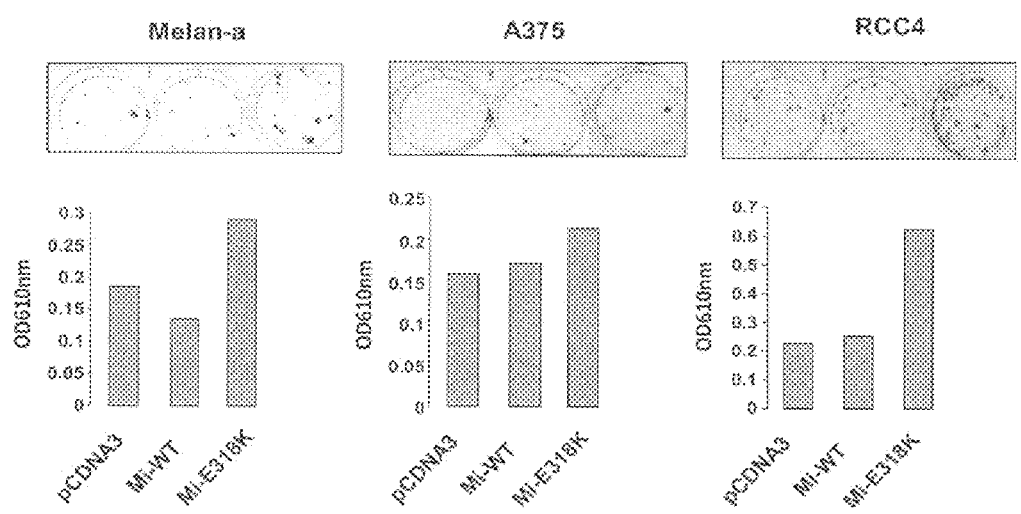
FIG. 7: The E318K mutation confers a growth advantage. Melanocytes from melan-a immortalized mice (left), the human metastatic melanoma A375 cell line (center) and human renal carcinoma RCC4 cells (right) were transfected with an empty vector, or a vector coding for wild-type MITF (Mi-WT) or mutant MITF (Mi-E318K). Photographs at 2 weeks (upper) and absorbance after crystal violet staining/destaining of the clones are shown.

The E318K Mutation Confers a Less Differentiated and More Highly Proliferative Cell Phenotype Production of pigment is one of the features of melanocyte differentiation, characterized by slower growth, in contrast to weakly pigmented cells which correlate closely with less differentiated, proliferative phenotypes. In addition, hypoxia and HIF1A sustain the survival, proliferation and transformation of melanocytes and the progression of melanoma. Accordingly, the inventors found that melanocytes isolated from skin biopsies of a patient with the germline mutation were less highly pigmented than melanocytes from two healthy mutation-negative donors, all three of which were Caucasian (FIG. 6). MITF transcription is modified by two receptor signaling pathways, including the melanocortin-1 receptor (MC1R). Lastly, compared with wild-type MITF, expression of E318K stimulated the growth of immortalized melanocytes (FIG. 7A, Melan-a), melanoma cells (FIG. 7B, A375) and VHL-deficient kidney cancer cells (FIG. 7C, RCC4). Taken together, the data suggest that the MITF E318K mutant confers a constitutive growth advantage.

Materials and Methods

Melarisk is a unique registry of melanoma-prone families (MELARISK) initiated in 1985 by Institut Gustave Roussy (Prof. Avril) and INSERM (Florence Demenais, U946), with participation of dermatologists (in particular, since 2005, Cochin University Hospital Center, Prof. Avril and Hospices Civils de Lyon, Prof. Thomas) and oncogeneticists. The biological materials are stored in the IGF cancer susceptibility Biobank (blood, frozen lymphocytes, lymphoblastic cell lines established by Genethon, DNA). Family, demographic, clinical and risk factor data for melanoma have been collected for several years now and are stored in a MySQL data base in INSERM unit U946.

Direct Sequencing of MITF

Primers used to sequence MITF are shown in the following table. The amplification protocol consisted of 35 cycles with 30-sec temperature steps at 94° C., 60° C. and 72° C.

PCR products were sequenced with the "Big Dye Terminator", version 3.0 (Applied Biosystems, Foster City, Calif.) on an ABI Prism© 3730 Genetic Analyzer (Applied Biosystems, Foster City, Calif.).

TABLE

Primer sequences for the MITF gene

| Amplified fragment | Sense Sequence 5' > 3' | Antisense Sequence 5' > 3' | Size of product (bp) |
|---|---|---|---|
| Exon 1a_part1 | SEQ ID NO 1 | SEQ ID NO 2 | 377 |
| Exon 1a_part2 | SEQ ID NO 3 | SEQ ID NO 4 | 394 |
| Exon 1b | SEQ ID NO 5 | SEQ ID NO 6 | 298 |
| Exon 1e | SEQ ID NO 7 | SEQ ID NO 8 | 232 |
| Exon 2/Exon 1c | SEQ ID NO 9 | SEQ ID NO 10 | 396 |
| Exon 1 (M) | SEQ ID NO 11 | SEQ ID NO 12 | 389 |
| Exon 2 | SEQ ID NO 13 | SEQ ID NO 14 | 426 |
| Exon 3 | SEQ ID NO 15 | SEQ ID NO 16 | 271 |
| Exon 4 | SEQ ID NO 17 | SEQ ID NO 18 | 257 |
| Exon 5 | SEQ ID NO 19 | SEQ ID NO 20 | 447 |
| Exon 6a/6b | SEQ ID NO 21 | SEQ ID NO 22 | 280 |
| Exon 7 | SEQ ID NO 23 | SEQ ID NO 24 | 320 |
| Exon 8 | SEQ ID NO 25 | SEQ ID NO 26 | 563 |
| Exon 9 | SEQ ID NO 27 | SEQ ID NO 28 | 544 |

Genotyping of the MITF E318K Mutation by PCR with a MGB Taqman Primer

PCR reactions were carried out with 10 ng of genomic DNA in the presence of 0.2 µmol/L of MGB Taqman primers, either (5'-VIC-ATC AAG CAA GAA CCC G-3'—SEQ ID No 29) which perfectly matches the wild-type MITF sequence or with (5'-6-FAM-CAA GCA AAA ACC CG-3'—SEQ ID No 30) which perfectly matches the MITF sequence coding the E318K mutation. Final concentrations of the other reagents were as follows: 1× Universal Master Mix (Applied), 0.4 µmol/L of sense primer (5'-TGCTCTCCA-GATTTGGTGAATCG-3'—SEQ ID No 31), 0.4 µmol/L of antisense primer (5'-GGTCTTGGCTGCAGTTCTCAA-3'—SEQ ID No 32). The size of the PCR amplicon was 67 bp. PCR cycling was carried out on a ABI™ 2720 thermocycler as follows: 95° C. for 15 min; 30 cycles at 95° C. for 15 sec and 60° C. for 1 min. Allelic discrimination was performed by a final fluorescence measurement on an ABI™ 7900HT Fast Real Time PCR system and analyzed with ABI™ SDS v2.3 software. Either wild-type or E318K DNA samples were included as controls in each genotyping experiment. Genotyped mutant samples were checked by direct sequencing using the protocol and primers described above for exon 9 of MITF.

Plasmids

The MITF M-form construct pCDNA3-Mi has been described previously (7). Mutations of MITF at K182R and/or E318K were generated using the QuickChange method (Stratagene) using the following sense primers with their reverse complements: Mi-K182R 5'-cttcccaacataagaagg-gagctcacagc-3' (SEQ ID No 33); MI-E318K 5'-ggatcatcaag-caaaaaccagttcttgag-3' (SEQ ID No 34). The presence of the mutations was confirmed by sequencing.

His-SUMO1 and His-HA-SUMO2 were kindly provided by M. A. Dejean and are described in the following publication (8).

Cotransfections and Immunoblots

HEK293 cells grown in 6-well dishes ($10^4$ cells/well) were transfected with the indicated plasmids (2 µg of total DNA/well) using FuGENE 6™ (Roche Applied Science). 48 hours later, cells were rinsed in PBS followed by lysis at 95° C. in 1× loading buffer (41.6 mM Tris, pH 6.8, 1.5% SDS, 6.7% glycerol) and boiling for an additional 5 minutes.

Proteins were resolved by electrophoresis in 10% SDS-polyacrylamide gels and transferred to PVDF membranes. Proteins were detected using ECL (Amersham) and anti-MITF (Abcam), anti-HA tag (Abcam), anti-SUMO1 (Santa Cruz Biotech) or anti-ERK2 (Santa Cruz Biotech) antibodies.

Reporter Assays

Human 501mel and mouse B16 cells were plated into 24-well plates ($25 \times 10^3$ cells/well) and, the following days, the cells were transiently transfected with 0.3 µg of reporter plasmid (pHIF1α and pMet), 0.05 µg of pCDNA2 MITF or empty pCDNA2 vector, 2 µl of lipofectamine reagent (Invitrogen) and 0.05 µg of pCMVβGal to control variability of transfection efficiency. Cells were lysed and assayed for luciferase and β-galactosidase activity 48 hours later. Transfections were performed at least in triplicate.

Immunofluorescence

HEK293 cells were plated on glass coverslips ($100 \times 10^3$ cells) in 6-well dishes and transfected with 3 µg of pCDNA3 MITF or empty pCDNA3 vector, using 10 µl of lipofectamine. 48 hours later, cells were fixed for 10 min with 4% paraformaldehyde in PBS, washed in PBS, and permeabilized for 2 min with 0.1% Triton X-100, 1% bovine serum albumin (BSA). Next, samples were washed once in PBS and treated with 50 mM $NH_4Cl$ for 2 min, then washed three times in PBS and stained for 1 hour with anti-MITF antibody (Abcam) in 1% BSA/PBS. Samples were then washed three times with PBS for 5 min and stained secondarily for 1 hour with Alexa-488 conjugated goat anti-mouse antibody (Molecular Probes) in 1% BSA. Cells were washed once in PBS, counterstained with 4,6-diamino-2-phenylindole (DAPI), washed 3 times in PBS and mounted using Fluromount-G (Southern Biotech, Birmingham Ala.). Cells were examined under a Zeiss Axiophot microscope with epifluorescence illumination.

Determination of Melanin Content

Approximately $6 \times 10^6$ melanocytes were pelleted by centrifugation at 1000 g for 5 min and washed twice in phosphate buffer. A fraction of the pellet was dissolved in 0.5% NaOH for 1 hour at 80° C. and optical density was measured at 405 nm. The other fraction was used to determine protein content by the BCA™ method (Pierce). Melanin content was corrected for protein concentration and expressed as a percentage of control cells (100%).

Test of Colony Formation

Human melanoma A375 cells and human kidney cancer RCC4 cells (80,000 per well) were transfected with a total of 3 µg DNA per well (wild-type MITF or E318K) and 10% pBABE-puro using Fugene (Roche). Puromycin (1 µg/ml) was added to the medium 48 hours after transfection. Fourteen days later the cells were fixed, stained with 0.4% crystal violet and plates were photographed. Cells were also destained with 10% acetic acid in PBS and cell counts were determined by measuring absorbance at 610 nm.

Immunohistochemistry

After dewaxing the coverslips and unmasking the antigens in hot Antigen Unmasking solution (Vector Laboratories), sections were permeabilized in 0.3% Triton/PBS for 15 min, then rinsed rapidly in PBS. After blocking endogenous peroxidases, the sections were saturated in PBS/1% BSA/5% goat serum for 30 min, then incubated overnight at 4° C. with the first anti-MITF antibody clone C5 (1:10 or 1:100 dilution) in PBS/1% BSA. After rinsing in PBS, sections were incubated with the second biotinylated antibody in PBS/1% BSA for 1 hour at room temperature. Sections were then rinsed in PBS and incubated in HRP Avidin/Biotin solution (ABC Elite kit, Vector Laboratories). After rinsing in PBS, the sections were revealed in the presence of a peroxidase substrate (VIP kit, Vector Laboratories). Finally, slides were mounted using Mountex (Cell Path).

REFERENCES

1. Levy, C., et al. (2006) *Trends Mol. Med.*, 12, 406-414.
2. Garraway, L. A., et al. (2005) *Nature*, 436, 117-122.
3. Kido, K., et al. (2009) *Cancer Sci.* 100, 1863-1869.
4. Larribere, L., et al. (2005) *Genes Dev.* 19, 1980-1985.
5. Chung, S. Y., et al. (2009) *Biosci. Biotechnol. Biochem.* 73, 1704-1710.
6. Halder, B., et al. (2009) *Carcinogenesis* 29, 129-138.
7. Bertolotto C, et al. (1998) *J. Cell Biol.* 142, 827-35.
8. Bischof O, et al. (2006) *Mol. Cell.* 22, 783-94.

The invention claimed is:

1. A method for determining whether a subject has a predisposition or a susceptibility to develop a cancer selected from a cutaneous malignant melanoma or a renal cancer, the method comprising (1) detecting in a biological sample obtained from said subject a germline mutation in microphthalmia-associated transcription factor (MITF) gene that causes the substitution of the E318 residue with a Lysine residue (the E318K mutation) in the MITF protein, said detecting step comprising contacting said sample with an oligonucleotide whose nucleotide sequence comprises the sequence of SEQ ID NO: 29 or contacting said sample with an oligonucleotide whose nucleotide sequence comprises the sequence of SEQ ID NO: 30 and an oligonucleotide whose nucleotide sequence comprises the sequence of SEQ ID NO: 29 and (2) diagnosing the predisposition or the susceptibility to develop cutaneous malignant melanoma or renal cancer in a subject identified as having the germline E318K mutation.

2. The method according to claim 1, wherein the cancer is the cutaneous malignant melanoma.

3. A method for determining whether a subject has a predisposition or a susceptibility to develop a cutaneous malignant melanoma or a renal cancer and treating said subject, the method comprising (1) detecting at the nucleic acid level by sequencing, selective hybridization and/or selective amplification the presence of a germline mutation in MITF gene that causes the substitution of the E318 residue with a Lysine residue (the E318K mutation) in the MITF protein, (2) diagnosing the predisposition or the susceptibility to develop cutaneous malignant melanoma or renal cancer in a subject identified as having the germline E318K mutation, and (3) administering an effective therapeutic dose of polyphenolic compounds to the subject identified as having the germline E318K mutation.

4. The method according to claim 3, wherein the polyphenolic compounds are polyphenolic compounds from fermented rice hulls or polyphenols from black tea.

5. A method for detecting a predisposition or a susceptibility of a subject to develop a cutaneous malignant melanoma or a renal cancer, the method comprising (1) assaying at the nucleic acid level for the presence or absence of a germline mutation in the microphthalmia-associated transcription factor (MITF) gene in a biological sample from the subject, wherein the germline mutation causes the substitution of the E318 residue with a Lysine residue (E318K mutation) in the MITF protein and said assaying step comprises contacting said sample with an oligonucleotide whose nucleotide sequence comprises the sequence of SEQ ID NO: 29, said assaying step comprises contacting said sample with an oligonucleotide whose nucleotide sequence comprises at least 14 contiguous bases of SEQ ID NO: 33, said assaying step comprises contacting said sample with an oligonucleotide whose nucleotide sequence comprises the sequence of SEQ ID NO: 33, said assaying step comprises contacting said sample with an oligonucleotide whose nucleotide sequence comprises at least eioht contiguous bases of SEQ ID NO: 30 or said assaying step comprises contacting said sample with an oligonucleotide whose nucleotide sequence comprises the sequence of SEQ ID NO: 30, (2) and diagnosing the predisposition or the susceptibility to develop cutaneous malignant melanoma or renal cancer in a subject whose biological sample has the presence of the germline E318K mutation.

6. The method according to claim 5, wherein said assaying step comprises contacting said sample with an oligonucleotide whose nucleotide sequence comprises at least eight contiguous bases of SEQ ID NO:30.

7. The method according to claim 5, wherein said assaying step comprises contacting said sample with an oligonucleotide whose nucleotide sequence comprises the sequence of SEQ ID NO:30.

8. The method according to claim 5, wherein said assaying step comprises contacting said sample with an oligonucleotide whose nucleotide sequence comprises at least 14 contiguous bases of SEQ ID NO:33.

9. The method according to claim 5, wherein said assaying step comprises contacting said sample with an oligonucleotide whose nucleotide sequence comprises the sequence of SEQ ID NO:33.

10. The method according to claim 5, wherein said assaying step comprises contacting said sample with an oligonucleotide whose nucleotide sequence comprises the sequence of SEQ ID NO: 29.

11. The method according to claim 1, wherein said detecting step comprises contacting said sample with an oligonucleotide whose nucleotide sequence comprises the sequence of SEQ ID NO: 29.

12. The method according to claim 1, wherein said detecting step comprises contacting said sample with an oligonucleotide whose nucleotide sequence comprises the sequence of SEQ ID NO: 30 and an oligonucleotide whose nucleotide sequence comprises the sequence of SEQ ID NO: 29.

13. The method according to claim 7, wherein said assaying step further comprises contacting said sample with an oligonucleotide whose nucleotide sequence comprises the sequence of SEQ ID NO:29.

* * * * *

UNITED STATES PATENT AND TRADEMARK OFFICE
CERTIFICATE OF CORRECTION

Page 1 of 1

PATENT NO.        : 9,194,003 B2
APPLICATION NO.   : 13/515984
DATED             : November 24, 2015
INVENTOR(S)       : Robert Ballotti et al.

It is certified that error appears in the above-identified patent and that said Letters Patent is hereby corrected as shown below:

IN THE SPECIFICATION

Column 16,
Line 33, "(Abeam)" should read --(Abcam)--.

IN THE CLAIMS

Column 45,
Line 33, "eioht" should read --eight--.

Signed and Sealed this
Twenty-ninth Day of March, 2016

Michelle K. Lee
*Director of the United States Patent and Trademark Office*